US009050020B2

(12) United States Patent
Abe et al.

(10) Patent No.: US 9,050,020 B2
(45) Date of Patent: Jun. 9, 2015

(54) ULTRASOUND DIAGNOSTIC APPARATUS AND IMAGE PROCESSING METHOD

(71) Applicants: Yasuhiko Abe, Otawara (JP); Shinichi Hashimoto, Otawara (JP)

(72) Inventors: Yasuhiko Abe, Otawara (JP); Shinichi Hashimoto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 25 days.

(21) Appl. No.: 13/684,722

(22) Filed: Nov. 26, 2012

(65) Prior Publication Data
US 2013/0137987 A1 May 30, 2013

(30) Foreign Application Priority Data

Nov. 30, 2011 (JP) ................................. 2011-262772
Oct. 16, 2012 (JP) ................................. 2012-228789

(51) Int. Cl.
*A61B 8/06* (2006.01)
*A61B 8/00* (2006.01)
*A61B 8/08* (2006.01)

(52) U.S. Cl.
CPC . *A61B 8/06* (2013.01); *A61B 8/461* (2013.01); *A61B 8/488* (2013.01); *A61B 8/5207* (2013.01); *A61B 8/5223* (2013.01); *A61B 8/0883* (2013.01); *A61B 8/463* (2013.01); *A61B 8/5284* (2013.01)

(58) Field of Classification Search
CPC ........ A61B 8/06; A61B 8/0883; A61B 8/461; A61B 8/463; A61B 8/488; A61B 8/5207; A61B 8/5223; A61B 8/5284
USPC .......................... 600/438, 441, 443, 453–457
See application file for complete search history.

(56) References Cited

U.S. PATENT DOCUMENTS

2011/0230764 A1* 9/2011 Baba et al. .................... 600/454

FOREIGN PATENT DOCUMENTS

JP 2010-68955 4/2010

* cited by examiner

*Primary Examiner* — Michael Rozanski
(74) *Attorney, Agent, or Firm* — Oblon, McClelland, Maier & Neustadt, L.L.P.

(57) ABSTRACT

An ultrasound diagnostic apparatus according to an embodiment includes a detector, a determination unit, a retention controller, and a display controller. The detector is configured to detect a peak flow velocity of blood flow velocities acquired from Doppler waveforms collected in a time-serial manner or a peak value of average flow velocities of the blood flow velocities as a representative flow velocity for each predefined period. The determination unit is configured to determine a maximum value in a predefined polarity of a plurality of representative flow velocities. The retention controller is configured to control a memory unit to retain maximum waveform information that is Doppler waveform information of Doppler waveforms collected for a period in which the maximum value was detected. The display controller is configured to control a display unit to display the maximum waveform information with Doppler waveform information having been collected by a present time point.

20 Claims, 18 Drawing Sheets

CONTINUOUS THREE HEART BEATS

ULTRASOUND DIAGNOSTIC APPARATUS AND IMAGE PROCESSING METHOD

CROSS-REFERENCE TO RELATED APPLICATIONS

This application is based upon and claims the benefit of priority from Japanese Patent Application No. 2011-262772, filed on Nov. 30, 2011; and Japanese Patent Application No. 2012-228789, filed on Oct. 16, 2012, the entire contents of all of which are incorporated herein by reference.

FIELD

Embodiments described herein relate generally to an ultrasonic diagnosis apparatus and an image processing method.

BACKGROUND

Conventionally, an ultrasonic diagnosis apparatus creates and displays blood flow information using Doppler signals extracted from ultrasonic reflected waves. The blood flow information created and displayed by the ultrasonic diagnosis apparatus generally includes color Doppler images and Doppler spectrums (Doppler waveforms). The Doppler waveforms are created by time-series plotting of blood flow velocities observed in an area set by an operator as a blood flow velocity observation range. Such a range is set by an operator referring to B-mode images, M-mode images, and color Doppler images. For example, in severity judgment of cardiac valve regurgitation or stenosis, the operator observes a color Doppler image, sets a collection range to an area determined as having regurgitation or a jet stream originating from stenosis, and collects Doppler waveforms using the CW (Continuous Wave) Doppler method or the PW (Pulsed Wave) Doppler method to perform Doppler measurement.

In severity judgment of regurgitation using Doppler measurement, detection of the largest part of a Doppler waveform, that is, the peak blood flow velocity (also referred to as the peak flow velocity) is important. In the CW Doppler method, the S/N (signal/noise) ratio of the largest part of a waveform is generally so low that the boundaries of the waveform tend to be unclear. Furthermore, an area of regurgitation often covers a small range, not a wide range. Thus, a sonographer, who is the operator of the ultrasound diagnostic apparatus, observes a Doppler waveform in real time while changing the way of putting an ultrasonic probe to receive reflected waves from the region of the regurgitation so that the "maximum" peak flow velocity can be obtained and verbally controlling breathing of the patient. The operator performs such an operation while observing and recording Doppler waveforms of multiple heart beats, judging if the "maximum" peak flow velocity has been obtained.

After the operator acknowledged that a Doppler waveform with the "maximum" peak flow velocity had been collected, the operator presses down the "Freeze button", reads out collected images from the memory, and refers to the collected images. At this point, the operator traces back the collected images to the past as necessary. Thereafter, the operator causes the Doppler waveform determined as of the "maximum" peak flow velocity to be displayed and performs various measurements for severity judgment of regurgitation or stenosis. For example, the operator manually traces the envelope of the Doppler waveform thus displayed, and the ultrasound diagnostic apparatus performs a measurement process based on the trace result. It should be noted that measurement values used for the severity judgment of regurgitation or stenosis include maximum flow velocity that is the "maximum" peak flow velocity, VTI (Velocity Time Integral), and pressure gradient suitably obtained by converting the maximum flow velocity using the Simplified Bernoulli Equation.

In recent years, ultrasound diagnostic apparatuses with functions to automatically trace the envelopes of Doppler waveforms have been developed. Furthermore, this automatic trace function has been used for calculating and outputting the average of measured values such as peak flow velocities at multiple heart beats (three to five heart beats, for example) in the past that include target Doppler waveforms. Although the automatic trace function may be performed by the CW Doppler method, in many cases it is applied to analysis in the PW Doppler method.

However, judgment over the collection of the Doppler waveform with the maximum peak flow velocity depends on the memory of the operator. Thus, in some cases actually, measurement is performed using a Doppler waveform that is not with the maximum peak flow velocity. In such cases, diagnosis accuracy for the severity judgment of regurgitation is decreased. Furthermore, since the recording period is specified for the collection of Doppler waveforms generally, the Doppler waveform with the maximum peak flow velocity cannot be displayed in some cases where the recording period expires. In such cases, recollection of Doppler waveforms becomes necessary, lengthening the examination time.

DETAILED DESCRIPTION

An ultrasound diagnostic apparatus according to an embodiment includes a detector, a determination unit, a retention controller, and a display controller. The detector is configured to detect a peak flow velocity of blood flow velocities acquired from Doppler waveforms collected in a time-serial manner or a peak value of average flow velocities of the blood flow velocities as a representative flow velocity for each predefined period. The determination unit is configured to determine a maximum value in a predefined polarity of a plurality of representative flow velocities by comparing values of representative flow velocities sequentially output from the detector. The retention controller is configured to control a predefined memory unit to retain maximum waveform information that is Doppler waveform information that is information on Doppler waveforms and is Doppler waveform information of Doppler waveforms collected for a period in which the maximum value was detected. The display controller is configured to control a predefined display unit to display the maximum waveform information with Doppler waveform information having been collected by a present time point.

Embodiments of an ultrasound diagnostic apparatus are described below in detail with reference to the accompanying drawings.

Figure 1:
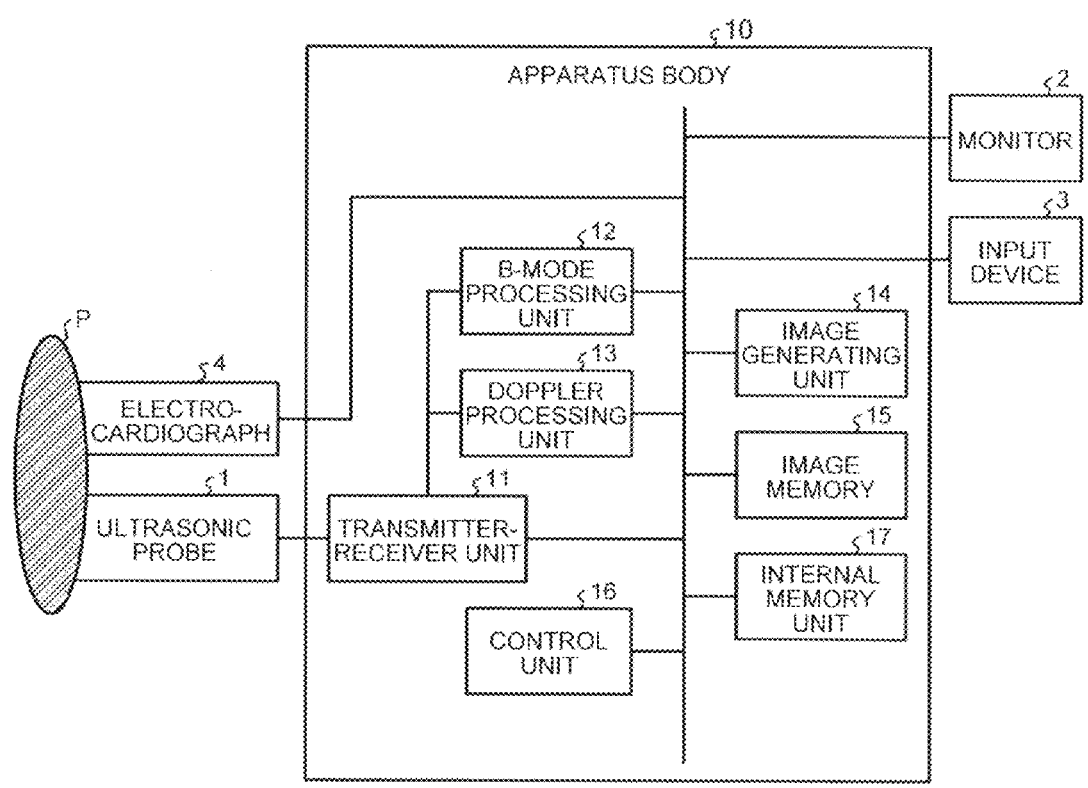
FIG. 1 is a diagram illustrating an example of a structure of an ultrasound diagnosis apparatus according to a first embodiment.

Firstly, a structure of an ultrasound diagnostic apparatus according to a first embodiment is described. FIG. 1 is a block diagram illustrating the structure of the ultrasound diagnostic apparatus according to the first embodiment. As illustrated in FIG. 1, the ultrasound diagnostic apparatus according to the present embodiment includes an ultrasonic probe 1, a monitor 2, an input device 3, an electrocardiograph 4, and an apparatus body 10.

The ultrasonic probe 1 includes a plurality of piezoelectric vibrators generating an ultrasonic wave based on a drive signal supplied from a transmitter-receiver unit 11 included in the apparatus body 10 described later. The ultrasonic probe 1 also receives a reflected wave from a subject P to convert it into an electrical signal. Furthermore, the ultrasonic probe 1 includes a matching layer and an acoustic lens provided to the piezoelectric vibrators and a backing material preventing an ultrasonic wave from traveling behind the piezoelectric vibrators, for example. The ultrasonic probe 1 is connected with the apparatus body 10 in a removable manner.

When ultrasonic waves are transmitted from the ultrasonic prove 1 to the subject P, the ultrasonic waves transmitted are continuously reflected on a plane of discontinuity of acoustic impedances in body tissues of the subject P and then received by the plurality of piezoelectric vibrators included in the ultrasonic probe 1 as reflected wave signals. The amplitude of the reflected wave signals received depends on the differences among the acoustic impedances on the plane of discontinuity on which the ultrasonic waves are reflected. It should be noted that when the ultrasonic pulses transmitted are reflected on the surface of a moving blood flow or cardiac wall, for example, the reflected wave signal undergoes a frequency shift (Doppler shift) depending on the velocity component against the ultrasound transmission direction of the moving body because of the Doppler effect.

The first embodiment is applicable to both the case where a subject P is two-dimensionally scanned with an ultrasonic probe 1 that is a one-dimensional ultrasonic probe with a plurality of piezoelectric vibrators arranged in line, and the case where a subject P is three-dimensionally scanned with an ultrasonic probe 1 that mechanically oscillates the piezoelectric vibrators of the one-dimensional ultrasonic probe 1 or by an ultrasonic probe 1 that is a two-dimensional ultrasonic probe with a plurality of piezoelectric vibrators two-dimensionally arranged in a reticular pattern.

Here, the ultrasound diagnostic apparatus according to the first embodiment collects Doppler waveforms in a range set on a color Doppler image (for example, a range gate or a scan line) after the color Doppler image is shot as described later. Thus, in the first embodiment, an ultrasonic probe 1 for performing the CFM (Color Flow Mapping) method may be replaced with an ultrasonic probe 1 for performing the CW (Continuous Wave) Doppler method or the PW (Pulsed Wave) Doppler method, depending on the type of the image to be collected.

The input device 3 includes a mouse, a keyboard, buttons, a panel switch, a touch command screen, a foot switch, and a trackball. The input device 3 receives various setting requests from an operator of the ultrasound diagnostic apparatus and transmits the setting requests thus received to the apparatus body 10.

For example, the operator performs the setting of a range gate using the trackball included in the input device 3. Furthermore, the operator stops collection of Doppler waveforms temporarily by pressing down the "Freeze button" included in the input device 3. The operator also sets the type of a measured value measured from a Doppler waveform. It should be noted that the details of the processes that the operator performs with the input device 3 are described later.

The monitor 2 displays a GUI (Graphical User Interface) for the operator of the ultrasound diagnostic apparatus to input various setting requests using the input device 3 and displays various images created in the apparatus body 10 and measurement results from the apparatus body 10, for example.

The electrocardiograph 4 is connected to the apparatus body 10 to acquire an ECG (electrocardiogram) of the subject P who undertakes an ultrasonic scanning. The electrocardiograph 4 transmits the ECG thus acquired to the apparatus body 10.

The apparatus body 10 is an apparatus that generates an ultrasonic wave image based on a reflected wave received by the ultrasonic probe 1. As illustrated in FIG. 1, the apparatus body 10 includes the transmitter-receiver unit 11, a B-mode processing unit 12, a Doppler processing unit 13, an image generating unit 14, an image memory 15, a control unit 16, and an internal memory unit 17.

The transmitter-receiver unit 11 includes a trigger generation circuit, a transmission delay circuit, and a pulsar circuit, and supplies a drive signal to the ultrasonic probe 1. The pulsar circuit repeatedly generates a rate pulse for forming a transmission ultrasound wave at a predetermined PRF (Pulse Repetition Frequency). The PRF is also referred to as a rate frequency. Further, the transmission delay circuit applies a delay period that is required to converge the ultrasound wave generated by the ultrasound probe 1 into the form of a beam and to determine transmission directionality and that corresponds to each of the piezoelectric vibrators, to each of the rate pulses generated by the pulsar circuit. The trigger generation circuit applies a drive signal (drive pulse) to the ultrasonic probe 1 at the timing based on the rate pulse. In other words, the transmission delay circuit arbitrarily adjusts the directions of the transmissions from the piezoelectric vibrator surfaces, by varying the delay periods applied to the rate pulses.

The transmitter-receiver unit 11 has functions capable of instantaneously changing transmission frequencies, transmission drive voltages, and the like in order to perform a predefined scan sequence based on an instruction from the control unit 16 described later. In particular, the transmission drive voltages can be changed with a linear amplifier type of transmission circuit capable of instantaneously changing values or a mechanism electrically switching over a plurality of power source units. These functions enable the transmitter-receiver unit 11 to transmit continuous or pulsed ultrasonic waves from the ultrasonic probe 1, for example.

Furthermore, the transmitter-receiver unit 11 includes an amplifier circuit, an A/D (analog/digital) converter, a reception delay circuit, and an adder, and generates reflected wave data through various processes on a reflected wave signal received by the ultrasonic probe 1. The amplifier circuit amplifies the reflected wave signal for each channel to perform a gain correction process. The A/D converter A/D-converts the reflected wave signal thus gain-corrected. The reception delay circuit provides digital data with a reception delay time required to determine reception directionality. The adder performs an adding process of the reflected wave signal thus provided with the reception delay time by the reception delay circuit to generate reflected wave data. The adding process performed by the adder emphasizes reflection components from the direction in accordance with the reception directionality of the reflected wave signal.

Here, the transmission delay time and the reception delay time are determined by the position (depth) of the transmission focus and the reception focus of an ultrasonic wave beam from an acoustic lens. The transmitter-receiver unit 11 controls transmission and reception directionalities in the transmission and reception of the ultrasonic wave in accordance with transmission and reception conditions such as the transmission delay time and the reception delay time. Furthermore, the transmitter-receiver unit 11 is capable of changing piezoelectric vibrators (diameters for transmission and reception) used for transmission and reception by the ultrasonic probe 1.

The B-mode processing unit 12 receives reflected wave data from the transmitter-receiver unit 11 and performs logarithmic amplification, envelope demodulation, and the like to generate data in which the intensity of a signal is represented by the brightness of its luminance (B-mode data).

The Doppler processing unit 13 extracts a Doppler shift through the frequency analysis of velocity information from the reflected wave data received from the transmitter-receiver unit 11 and extracts blood flows, tissues, and contrast agent echo components influenced by the Doppler effect resulting from the use of the Doppler shift, generating data (Doppler data) formed of extraction of moving body information such as average velocity, variance, and power at many points.

The B-mode processing unit 12 and the Doppler processing unit 13 according to the present embodiment may be applied to the case where both two-dimensional and three-dimensional reflected wave data can be processed.

The image generating unit 14 generates an ultrasonic image from the data generated by the B-mode processing unit 12 and the Doppler processing unit 13. In other words, the image generating unit 14 generates a B-mode image in which the intensity of reflected waves is represented by the luminance thereof from B-mode data generated by the B-mode processing unit 12. Furthermore, the image generating unit 14 generates a color Doppler image serving as an average velocity image, a dispersion image, a power image, or an image of combination of these images representing moving body information (blood flow information and moving tissue information) from the Doppler data generated by the Doppler processing unit 13.

Here, the image generating unit 14 generally converts (scan-converts) a row of scan line signals from an ultrasonic scanning into a row of scan line signals in a video format represented by television, for example, to generate an ultrasonic wave image as an image for display. Specifically, the image generating unit 14 generates an ultrasonic wave image as an image for display through coordinate conversion in accordance with the scanning form of the ultrasonic wave from the ultrasonic probe 1. Furthermore, the image generating unit 14 performs various types of image processing besides the scan conversion. For example, the image generating unit 14 performs image processing regenerating an image with an average luminance using a plurality of scan-converted image frames (smoothing process) and image processing using a differentiation filter within the image (edge emphasis process).

Furthermore, the image generating unit 14 generates a Doppler waveform created by time-series plotting of blood flow velocity information from the Doppler data generated by the Doppler processing unit 13.

The image generating unit 14 is also capable of generating a composite image in which an ultrasonic wave image (B-mode image, color Doppler image, Doppler waveform, and the like) is combined with character information, scales, body marks, and the like of various parameters.

The image memory 15 is a memory that stores therein various images generated by the image generating unit 14. The image memory 15 is also capable of storing therein data generated by the B-mode processing unit 12 and the Doppler processing unit 13.

The internal memory unit 17 stores therein various data such as a control program for performing transmission and reception of an ultrasonic wave, image processing, and display processing, diagnostic information (patients' IDs and doctors' opinions, for example), a diagnostic protocol, various body marks, and the like. The internal memory unit 17 is also used for storing therein images stored in the image memory 15 as necessary. Furthermore, data stored in the internal memory unit 17 may be transmitted to an external peripheral device via an interface (not illustrated).

The control unit 16 controls the overall processes performed by the ultrasound diagnostic apparatus. Specifically, the control unit 16 controls processes performed by the transmitter-receiver unit 11, the B-mode processing unit 12, the Doppler processing unit 13, and the image generating unit 14 based on various setting requests input by an operator via the input device 3 and various control programs and data read out from the internal memory unit 17. The control unit 16 also controls to display an ultrasonic wave image stored in the image memory 15 and a GUI for specifying various processes performed by the image generating unit 14, for example, on the monitor 2. Furthermore, the control unit 16 uses a computer program for measurement read out from the internal memory unit 17 to perform measurement processes using various images generated by the image generating unit 14, for example.

The overall structure of the ultrasonic diagnostic apparatus according to the first embodiment has been described above. Based on such a structure, the ultrasonic diagnostic apparatus according to the first embodiment generates Doppler waveforms in the range set by an operator and displays the Doppler waveforms thus generated. The operator uses a desired Doppler waveform selected from the Doppler waveforms thus displayed to perform settings for various measurement processes.

Figure 2:
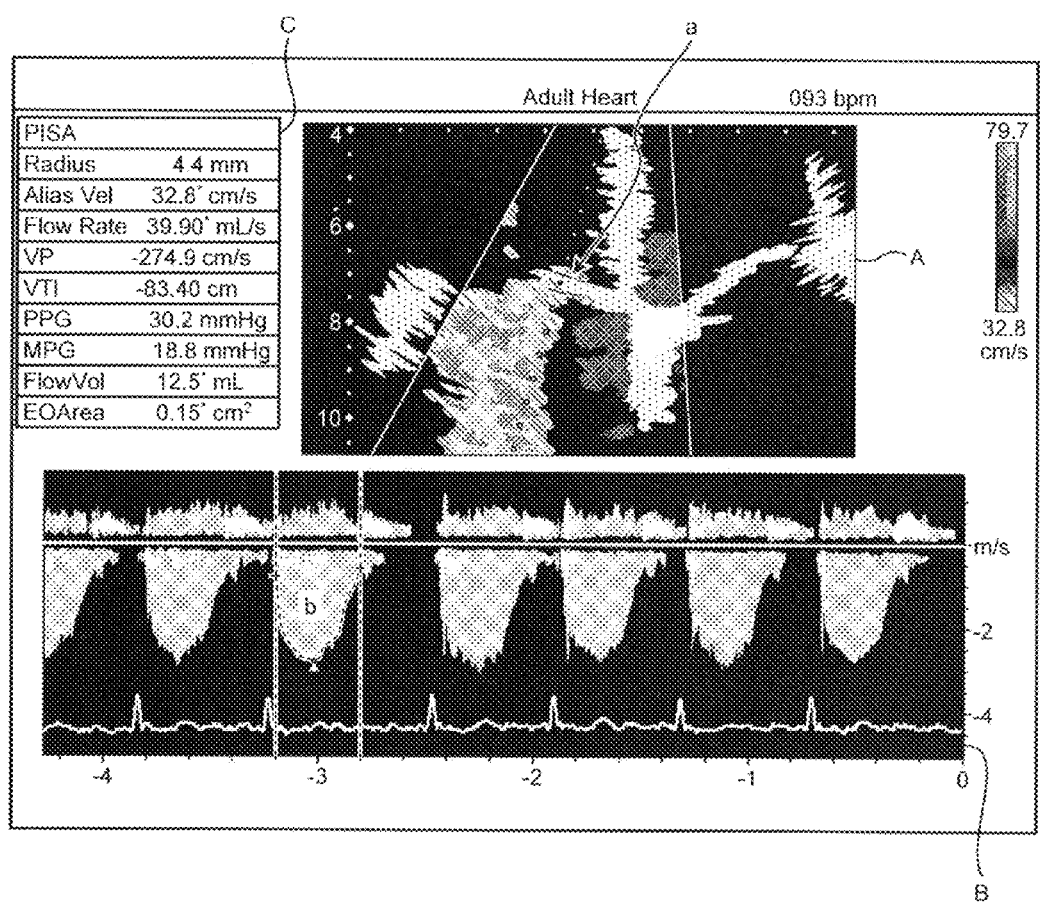
FIG. 2 is a diagram illustrating an example of conventional Doppler measurement.

For example, in severity judgment of cardiac valve regurgitation or stenosis, an operator observes a color Doppler image, sets a range gate to an area determined as having regurgitation or a jet stream originating from stenosis, and collects Doppler waveforms using the CW (Continuous Wave) Doppler method or the PW (Pulsed Wave) Doppler method to perform Doppler measurement. An example of Doppler measurement performed using a conventional ultrasound diagnostic apparatus is described below with reference to FIG. 2, and thereafter, Doppler measurement performed with the diagnostic apparatus according to the first embodiment is described. FIG. 2 is a diagram illustrating an example of conventional Doppler measurement.

For example, an operator sets a range in which the CFM method is performed on a B-mode image generated by the image generating unit 14. Based on this, the control unit 16 performs the CFM method in the range set by the operator by controlling each processing unit. Thereafter, the control unit 16 controls the image generating unit 14 to generate a superimposed image A with a color Doppler image in the set range superimposed on the B-mode image. Furthermore, the control unit 16 controls the monitor 2 to display the superimposed image A as illustrated in FIG. 2. The operator refers to the color Doppler image on the superimposed image A to set a range gate a near the cardiac valve (aortic valve or mitral valve) determined as having regurgitation or a jet stream originating from stenosis. Thereafter the operator gives an instruction to collect Doppler waveforms at the range gate a by the CW method, for example. In the CW method, a focus point is set at the range gate a, for example, and the Doppler waveforms collected will be waveforms based on reflected wave signals for all scan lines passing through the range gate a.

The control unit 16 controls the image generating unit 14 to generate Doppler waveforms from Doppler data generated by the Doppler processing unit 13. Furthermore, the control unit 16 controls the monitor 2 to display the Doppler waveforms generated by the image generating unit 14 in a time-serial manner. For example, the control unit 16 sets the current collection time point to "0" and controls to display the Doppler waveforms so that blood flow velocities newly calculated are displayed in an updated manner along the time axis that indicates past collection time points by negative. It should be noted that the control unit 16 also controls to display an ECG with the Doppler waveforms in a state that the time axis of the Doppler waveforms and the time axis of the ECG are fitted.

In severity judgment of regurgitation or stenosis using Doppler measurement, detection of the largest part of a Doppler waveform, that is, the peak blood flow velocity (also referred to as the peak flow velocity) is important. In the CW Doppler method, the S/N (signal/noise) ratio of the largest part of a waveform is generally so low that the boundaries of the waveform tend to be unclear. Furthermore, an area of regurgitation or a jet stream originating from stenosis often covers a small range, not a wide range. Thus, an operator observes a Doppler waveform in real time while changing the way of putting the ultrasonic probe 1 to receive reflected waves from the region of the regurgitation so that the "maximum" peak flow velocity can be obtained and verbally controlling breathing of the patient. The operator performs such an operation while observing and recording Doppler waveforms of multiple heart beats, judging if the "maximum" peak flow velocity has been obtained.

After the operator acknowledged that a Doppler waveform with the "maximum" peak flow velocity had been collected, the operator presses down the "Freeze button", reads out collected images from the image memory 15, and traces back the collected images to the past by operating a trackball, for example. Thereafter, the operator causes the monitor 2 to display Doppler waveforms in a continuous heart beat period including the Doppler waveform determined as of the "maximum" peak flow velocity, that is, the image data B of the Doppler waveform illustrated in FIG. 2. In the example illustrated in FIG. 2, the Doppler waveform b at three seconds before the "Freeze button" is pressed down, that is, in the heart beat period near "−3 seconds" in time in the image data B should be the Doppler waveform that the operator determined as of the "maximum" peak flow velocity.

The operator manually sets the envelope of the Doppler waveform b by manually tracing the waveform boundary of the Doppler waveform b using a mouse included in the input device 3, for example. Thereafter, the operator specifies the type of a measured value using the input device 3 to perform measurement processes performed by the control unit 16. The control unit 16 controls to display measured values obtained from measurement results in the measured value display area C illustrated in FIG. 2 in a table format, for example.

For example, if a maximum flow velocity (VP, unit: cm/s) that is a value for the "maximum" peak flow velocity is set as a measured value, the control unit 16 measures the maximum flow velocity from the envelope of the Doppler waveform b as "−274.9". Thereafter, the control unit 16 controls to display the measured value "VP: −274.9" in the measured value display area C as illustrated in FIG. 2.

Furthermore, if a VTI (Velocity Time Integral, unit: cm) that is a time integration value for a blood flow velocity is set as a measured value, for example, the control unit 16 measures the VTI from the envelope of the Doppler waveform b as "−83.40". Thereafter, the control unit 16 controls to display the measured value "VTI: −83.40" in the measured value display area C as illustrated in FIG. 2.

Furthermore, if a PPG (Peak Pressure Gradient, unit: mmHg) that is a PG (Pressure Gradient) calculated from a peak flow velocity using the Simplified Bernoulli Equation and that is a value for a pressure gradient for a maximum flow velocity is set as a measured value, for example, the control unit 16 measures the PPG from the maximum flow velocity (peak flow velocity of the Doppler waveform b) as "30.2". Thereafter, the control unit 16 controls to display the measured value "PPG: 30.2" in the measured value display area C as illustrated in FIG. 2.

Furthermore, if an MPG (Mean Pressure Gradient, unit: mmHg), which is an average of pressure gradients in a three heart beat period, is set as a measured value, for example, the control unit 16 calculates the average of the pressure gradients of the Doppler waveform b (peak pressure gradient) and the pressure gradients of two Doppler waveforms prior to the Doppler waveform b as "18.8". Thereafter, the control unit 16 controls to display the measured value "MPG: 18.8" in the measured value display area C as illustrated in FIG. 2. In addition, if an average flow velocity (time mean velocity: VM, unit: cm/s) is set as a measured value, the average of the peak flow velocity (maximum flow velocity) of the Doppler waveform b and the peak flow velocities of two Doppler waveforms prior to the Doppler waveform b is calculated, and the average flow velocity is displayed in the measured value display area C (not illustrated in FIG. 2).

In the example illustrated in FIG. 2, the control unit 16 performs various measurements by the PISA (Proximal Isovelocity Surface Area) method besides the above-described measurements and displays measurement results thereof in the measured value display area C. In the example illustrated in FIG. 2, the radius of a PISA hemisphere, the alias velocity of the surface of the PISA hemisphere, a surface flow rate per unit time on the PISA hemisphere, a surface flow volume on the PISA hemisphere, an effective orifice area (EOArea), and the like are measured by the control unit 16 to be displayed in the measured value display area C.

However, in such a conventional Doppler measurement that is performed with the workflow described above with reference to FIG. 2, judgment over the collection of the Doppler waveform with the maximum peak flow velocity depends on the memory of the operator. Thus, in some cases actually, measurement is performed using a Doppler waveform that is not with the maximum peak flow velocity. Furthermore, since the recording period is specified for the collection of Doppler waveforms generally, the Doppler waveform with the maximum peak flow velocity cannot be displayed in some cases where the recording period expires. In such cases, recollection of Doppler waveforms becomes necessary, lengthening the examination time. Such a problem arises also in the case where the control unit 16 is equipped with functions to automatically trace the envelopes of Doppler waveforms for which development has been promoted in recent years.

In the first embodiment, in order to alleviate the burden on the operator collecting Doppler waveforms with the maximum peak flow velocity, the control unit 16 performs the following processes. It should be noted that the processes described below are performed after the start of the collection of the Doppler waveforms on the scan lines set by the operator through the CW method, for example. In addition, the present embodiment can be applied to the case where the collection of the Doppler waveforms in the range gate set by the operator using the PW method.

Figure 3:
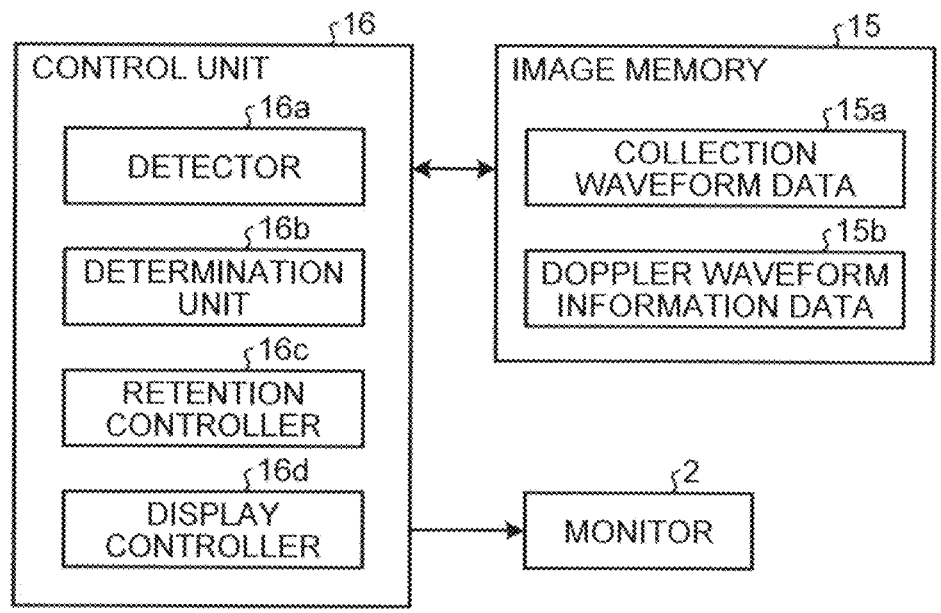
FIG. 3 is a diagram illustrating an example of a structure of a control unit according to the first embodiment.

FIG. 3 is a block diagram illustrating an example of the structure of the control unit according to the first embodiment. For example, the control unit 16 includes a detector 16a, a determination unit 16b, a retention controller 16c, and a display controller 16d as illustrated in FIG. 3. Furthermore, in the first embodiment, the image memory 15 is set with two memory areas for collection waveform data 15a and Doppler waveform information data 15b as illustrated in FIG. 3. The collection waveform data 15a is an area for temporarily storing therein collected Doppler waveforms. The Doppler waveform information data 15b is a memory area for temporarily retaining Doppler waveform information that is information on Doppler waveforms under the control of the retention controller 16c described later.

Figure 4:
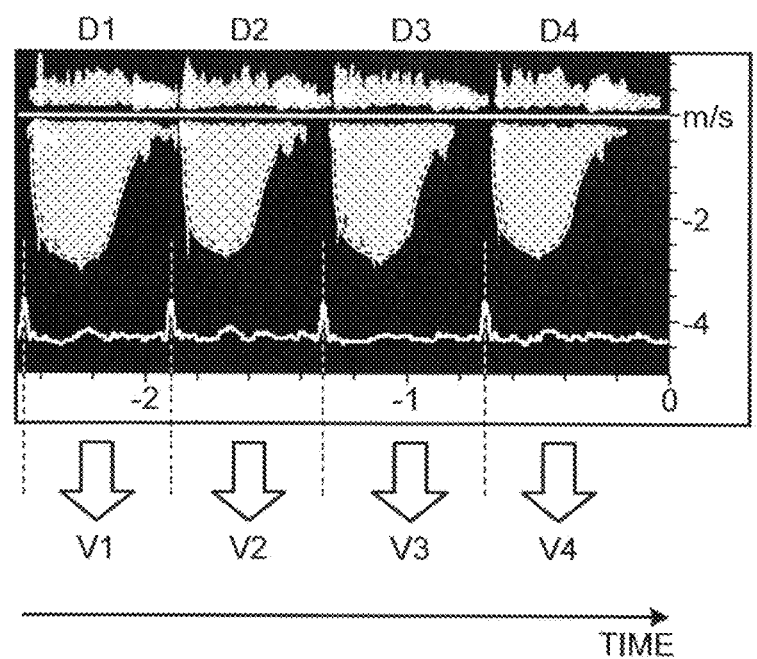
FIG. 4 is a diagram illustrating an example of a process performed by a detector.

The detector 16a detects a peak flow velocity of the flow velocities acquired from Doppler waveforms collected in a time-serial manner (envelope of a spectrum) or a peak value in a predefined period related to averages of the blood flow velocities (gravity center of the spectrum) as a representative flow velocity for each predefined period. In the present embodiment in which the CW method is performed, the detector 16a detects a peak value of the peak blood flow velocities from the Doppler waveforms collected in a time-serial manner as a representative value for each predefined period. In the present embodiment, a one heart beat period is set as the predefined period. In other words, the detector 16a detects a peak value in one heart beat related to the peak blood flow velocities from the Doppler waveforms collected in a time-serial manner for each period of one heart beat. Specifically, the detector 16a detects a representative flow velocity by detecting the envelope or the gravity center of each Doppler waveform. In the present embodiment, the detector 16a detects the peak flow velocity by detecting the envelope of each Doppler waveform. FIG. 4 is a diagram illustrating an example of the process performed by the detector.

In the collection waveform data 15a illustrated in FIG. 3, Doppler waveforms generated by the image generating unit 14 are sequentially stored in a time-serial manner under the control of the control unit 16. The control unit 16 also stores an ECG acquired by the electrocardiograph 4, together with the Doppler waveforms, in the collection waveform data 15a.

The detector 16a acquires a reference time phase of a heart beat from the ECG. For example, the detector 16a acquires an end-diastolic time phase corresponding to an R-wave of the ECG to acknowledge sections in the heart beat period. Thus, the detector 16a acknowledges a "Doppler waveform D1" that is a Doppler waveform in a one heart beat period and auto-traces the envelope of the "Doppler waveform D1", thereby detecting a peak value "V1" of peak flow velocities of the "Doppler waveform D1" as illustrated in FIG. 4. Similarly, the detector 16a acknowledges a "Doppler waveform D2" that is a Doppler waveform in a one heart beat period that was collected following the "Doppler waveform D1" and auto-traces the envelope of the "Doppler waveform D2", thereby detecting a peak value "V2" of peak flow velocities of the "Doppler waveform D2" as illustrated in FIG. 4. By repeating such processes, the detector 16a sequentially detects a peak value "V3" of peak flow velocities of the "Doppler waveform D3" and a peak value "V4" of peak flow velocities of the "Doppler waveform D4" as illustrated in FIG. 4.

The detector 16a may auto-trace the envelopes of Doppler waveforms sequentially stored in the collection waveform data 15a and acknowledge sections in the heart beat periods based on the trace results. In addition, in Doppler waveforms collected through the PW method, the distribution of velocity components in a range gate is represented by the width of a spectrum. Thus, if the PW method is performed, the detector 16a detects a peak value of peak flow velocities obtained from Doppler waveforms or a peak value of average flow velocities serving as the gravity center of the width of the Doppler waveforms as a representative flow velocity for each predefined period. In the PW method, whether the representative flow velocity should be the peak flow velocity or the average flow velocity is optionally changed by the operator, for example.

Figure 5:
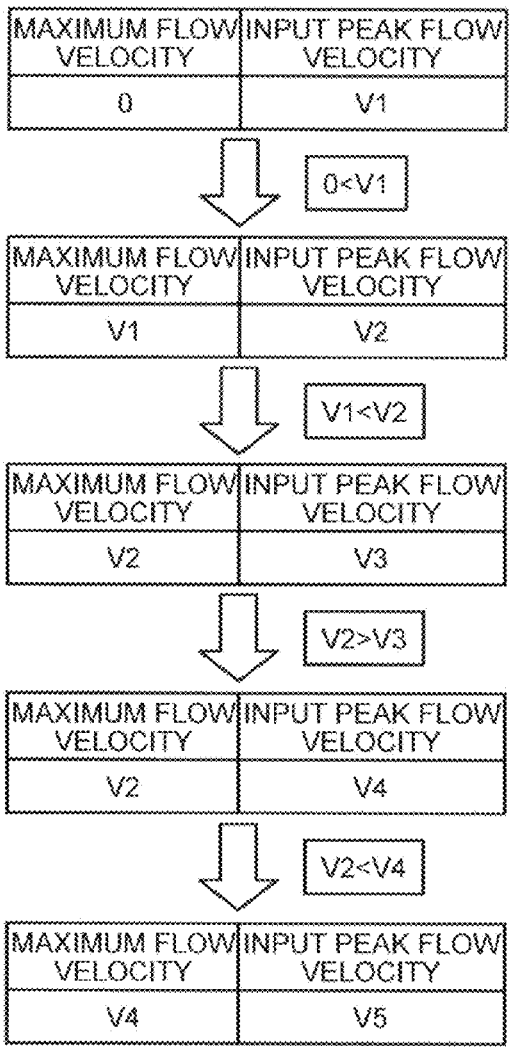
FIG. 5 is a diagram illustrating an example of a process performed by a determination unit according to the first embodiment.

The determination unit 16b illustrated in FIG. 3 compares the values of a plurality of representative flow velocities sequentially output from the detector 16a, thereby determining a maximum value in a predefined polarity out of the representative flow velocities. In the present embodiment, the determination unit 16b compares the values of a plurality of peak flow velocities sequentially output from the detector 16a, thereby determining a maximum value out of the peak flow velocities. Specifically, the determination unit 16b determines the maximum value (maximum flow velocity) of the peak flow velocities at the present time point in a predefined polarity. It should be noted that in the PW method, if the detector 16a detects an average flow velocity as a representative flow velocity, the determination unit 16b determines the maximum value in a predefined polarity out of a plurality of average flow velocities. For example, for the polarity of the representative flow velocities, the polarity of blood flows toward the ultrasonic probe 1 is defined as positive, and the polarity of blood flows directed away from the ultrasonic probe 1 is defined as negative. For example, if the predefined polarity is set as "positive", the determination unit 16b determines the maximum value of representative flow velocities in the positive polarity. Alternatively, if the predefined polarity is set as "negative", for example, the determination unit 16*b* determines the maximum value of representative flow velocities in the negative polarity. Furthermore, if the predefined polarity is set as "positive and negative", for example, the determination unit 16*b* determines the absolute maximum value of representative flow velocities. The predefined polarity may be set by the operator or by default. FIG. 5 is a block diagram illustrating an example of the processes performed by the determination unit according to the first embodiment.

As illustrated in FIG. 5, the determination unit 16*b* sets the initial value for the maximum flow velocity to "0" and compares the initial value "0" and "V1" that is the peak flow velocity (input peak flow velocity) initially received from the detector 16*a*. It should be noted that in the following description, the determination unit 16*b* acknowledges the absolute value of a value received from the detector 16*a* as the "input peak flow velocity" to perform processes for determining the maximum flow velocity.

The determination unit 16*b* updates the maximum flow velocity to "V1" because "0<V1" as indicated in FIG. 5. Thereafter, the determination unit 16*b* compares "input peak flow velocity: V2" and "maximum flow velocity: V1" and updates the maximum flow velocity to "V2" because "V1<V2" as indicated in FIG. 5. The determination unit 16*b* compares "input peak flow velocity: V3" and "maximum flow velocity: V2" and determines the maximum flow velocity as "V2" without updating because "V2>V3" as indicated by FIG. 5. Thereafter, the determination unit 16*b* compares "input peak flow velocity: V4" and "maximum flow velocity: V2" and updates the maximum flow velocity to "V4" because "V2<V4" as indicated in FIG. 5. Furthermore, the determination unit 16*b* compares "input peak flow velocity: V5" and "maximum flow velocity: V4".

The determination unit 16*b* determines the maximum flow velocity at the present time point by sequentially performing the comparison processes illustrated in FIG. 5.

The retention controller 16*c* illustrated in FIG. 3 controls the image memory 15 (Doppler waveform information data 15*b*) to retain maximum waveform information that is Doppler waveform information, that is, information of a Doppler waveform and also is Doppler waveform information of the Doppler waveform collected in the period in which the maximum value was detected. In the present embodiment, because the predefined period is a one heart beat period, the retention controller 16*c* controls the image memory 15 (Doppler waveform information data 15*b*) to retain Doppler waveform information of the Doppler waveforms in the one heart beat period of which the representative flow velocity (peak flow velocity in the present embodiment) at the present time point is the maximum as maximum waveform information. Here, the Doppler waveform information as the maximum waveform information includes image data of the Doppler waveforms corresponding to the Doppler waveform information in question and measured values measured from the Doppler waveforms in question. Furthermore, the measured values include at least one of a maximum flow velocity (VP), a peak pressure gradient (PPG), a mean pressure gradient (MPG), an average flow velocity (VM), and a velocity time integral (VTI). Here, the maximum value for VP and PPG refers to a peak value in a one heart beat period, and "P" in VP and PPG represents "peak". In addition, the average for MPG and VM refers to an average in a one heart beat period, and "M" in MPG and VM represents "mean". The above-described measured value is calculated using envelopes detected by the detector 16*a*. In the present embodiment, for example, the detector 16*a* performs calculation processes of measured values. It should be noted that the present embodiment may be applied to both the case where calculation processes of measured values other than VP are performed by the determination unit 16*b* and the case where calculation processes of measured values other than VP are performed by a measurement processing unit separately installed.

Figure 6:
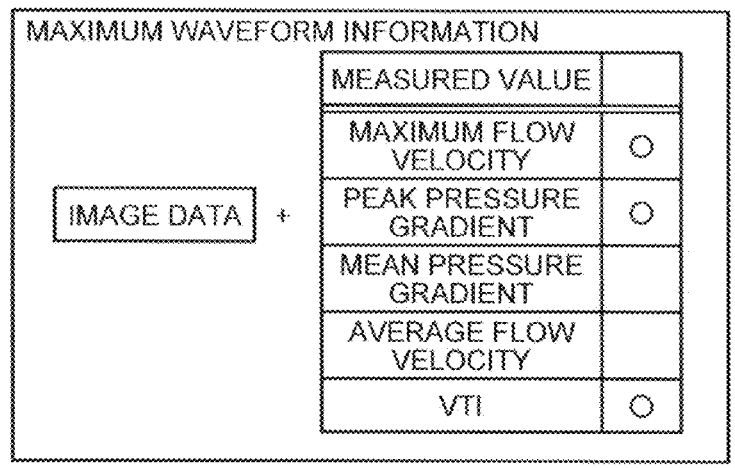
FIG. 6 is a diagram illustrating a setting example of maximum waveform information.
Figure 7:
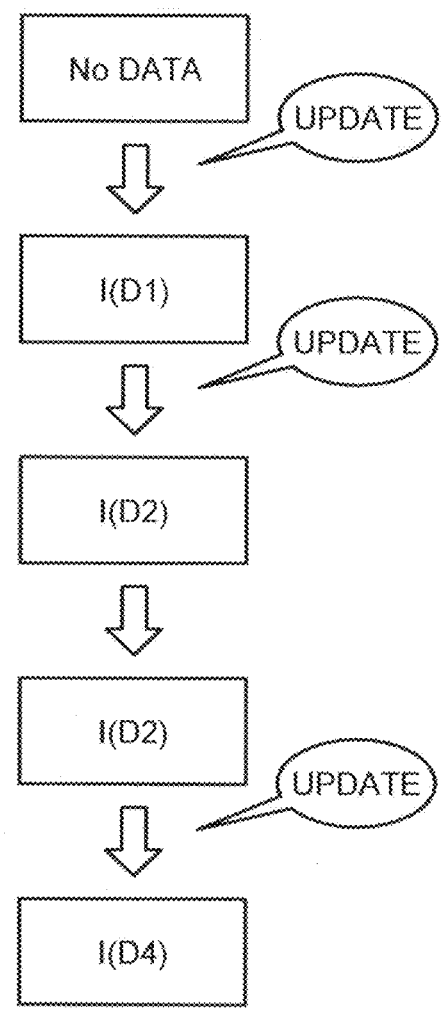
FIG. 7 is a diagram illustrating an example of a process performed by a retention controller according to the first embodiment.

Such maximum waveform information is preset by an operator before collection of Doppler waveforms, for example. FIG. 6 is a diagram illustrating an example of setting the maximum waveform information. In the example illustrated in FIG. 6, the operator selects three measured values of "maximum flow velocity, peak pressure gradient, VTI" as the maximum waveform information with image data of the Doppler waveforms. If such setting is performed, the retention controller 16*c* controls the Doppler waveform information data 15*b* to retain "image data" of the Doppler waveforms of which the maximum flow velocities have been measured by the present time point and "VP, PPG, VTI" measured from the Doppler waveforms in question as the maximum waveform information. FIG. 7 is a diagram illustrating an example of processes performed by the retention controller according to the first embodiment.

The example illustrated in FIG. 7 represents the processes performed by the retention controller 16*c* based on the results from the processes performed by the determination unit 16*b* illustrated in FIG. 5. It should be noted that in FIG. 7, the maximum waveform information in the case where the Doppler waveform of which the maximum flow velocity has been measured is "D1" is represented as "I(D1)".

First, from the start of the Doppler waveform collection until the time point at which Doppler waveforms for a one heart beat period have not been collected, the Doppler waveform information data 15*b* is in a "No DATA" state as illustrated in FIG. 7. Next, if the maximum flow velocity is updated to "V1", the retention controller 16*c* updates data to be retained by the Doppler waveform information data 15*b* from "No DATA" to "I(D1)" as illustrated in FIG. 7. Next, if the maximum flow velocity is updated to "V2", the retention controller 16*c* updates the data to be retained by the Doppler waveform information data 15*b* from "I(D1)" to "I(D2)" as illustrated in FIG. 7.

Next, if the maximum flow velocity is not updated from "V2", the retention controller 16*c* maintains the data to be retained by the Doppler waveform information data 15*b* of "I(D2)" as illustrated in FIG. 7. Next, if the maximum flow velocity is updated to "V4", the retention controller 16*c* updates the data to be retained by the Doppler waveform information data 15*b* from "I(D2)" to "I(D4)" as illustrated in FIG. 7.

Figure 8:
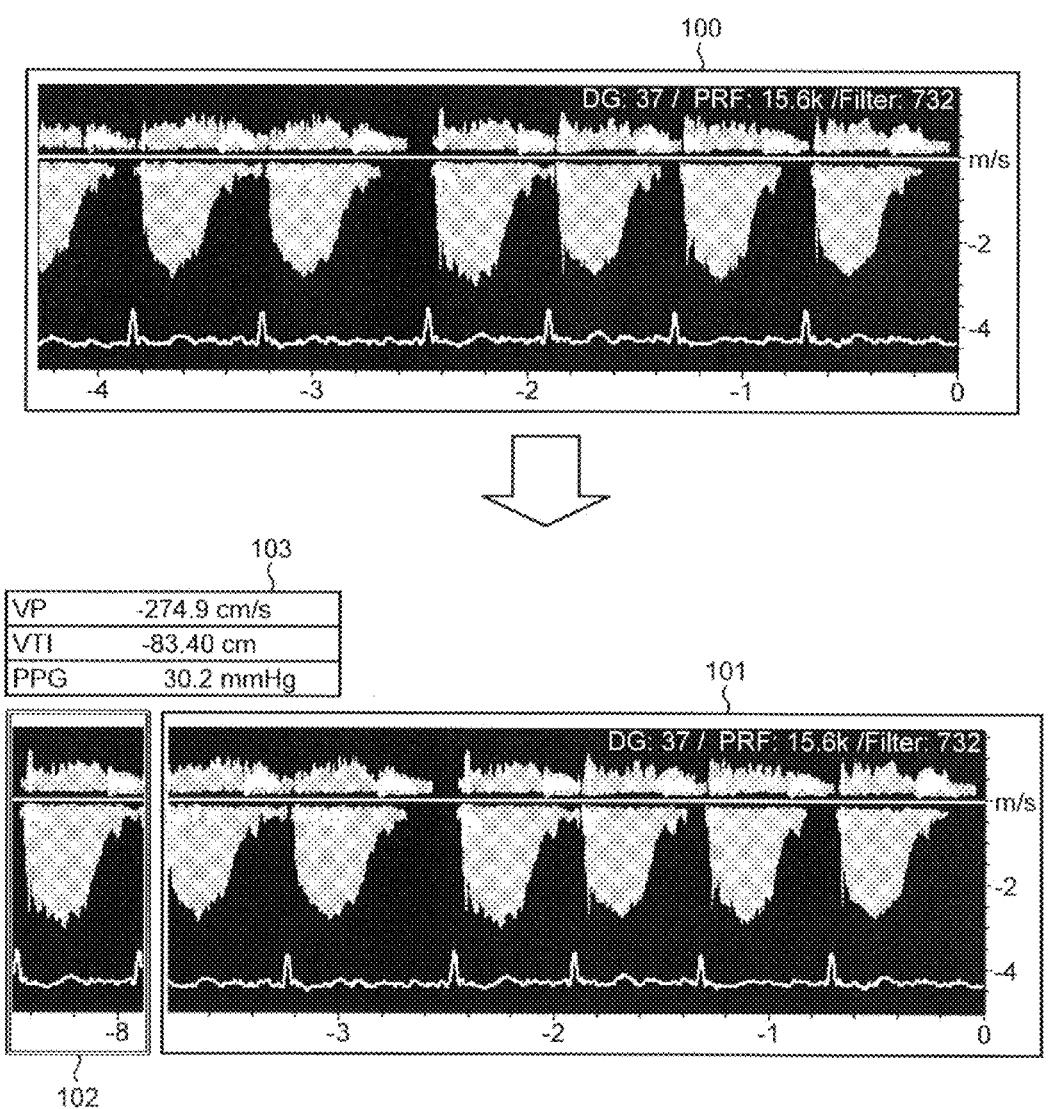
FIG. 8 is a diagram illustrating an example of a display process performed by a display controller according to the first embodiment.

The display controller 16*d* illustrated in FIG. 3 controls to simultaneously display the maximum waveform information with Doppler waveform information that has been collected by the present time point on the monitor 2. In the first embodiment, the display controller 16*d* sets the same scale for the display scale for image data of Doppler waveforms corresponding to the maximum waveform information and the display scale for image data of Doppler waveforms that have been collected by the present time point and controls to display various image data in parallel. FIG. 8 is a diagram illustrating an example of display processes performed by the display controller according to the first embodiment.

For example, from the start of the Doppler waveform collection until the time point at which Doppler waveforms for a one heart beat period have not been collected, the display controller 16*d* controls a waveform display area 100 to display the latest Doppler waveform and image data of a group of Doppler waveforms for a period of a plurality of heart beats collected immediately before the Doppler waveform in question as image data of Doppler waveforms that have been collected by the present time point as illustrated in the upper diagram in FIG. 8. In the example illustrated in FIG. 8, the waveform display area 100 displays image data for a group of Doppler waveforms for a period of about 6.5 heart beats (for about 4.2 seconds).

Once the data is stored in the Doppler waveform information data 15b under the control of the retention controller 16c, the display controller 16d changes the waveform display area 100 into two areas: a latest waveform display area 101 and a maximum waveform display area 102. Here, the scales of the vertical axis and the horizontal axis in the latest waveform display area 101 and the maximum waveform display area 102 should be the same as illustrated in the diagram in the lower part of FIG. 8.

The display controller 16d controls to display image data of the latest Doppler waveform and a group of Doppler waveforms for a period of a plurality of heart beats collected immediately before the Doppler waveform in question in the latest waveform display area 101 as image data of the Doppler waveforms that have been collected by the present time point. In the example illustrated in FIG. 8, image data of a group of Doppler waveforms for a period of about six heart beats (about 3.8 seconds) is displayed in the latest waveform display area 101.

Furthermore, the display controller 16d displays image data of the maximum waveform information in the maximum waveform display area 102. In other words, the maximum waveform display area 102 displays image data of the Doppler waveform of which the maximum flow velocity at the present time point was measured. Specifically, the image data displayed in the maximum waveform display area 102 is updated every time the maximum flow velocity at the present time point is updated.

The display controller 16d also newly sets a measured value display area 103 for displaying a measured value included in the maximum waveform information as illustrated in the diagram in the lower part of FIG. 8. The measured value display area 103 displays a measured value measured from the Doppler waveform of which the maximum flow velocity at the present time point. For example, as illustrated in the lower diagram in FIG. 8, the measured value display area 103 displays "VP: −274.9 cm/s, VTI: −83.40 cm, PPG: 30.2 mmHg" measured from the Doppler waveform displayed in the maximum waveform display area 102 in a table format. It should be noted that measured values displayed in the maximum waveform display area 102 are updated every time the maximum flow velocity at the present time is updated.

Figure 9A:
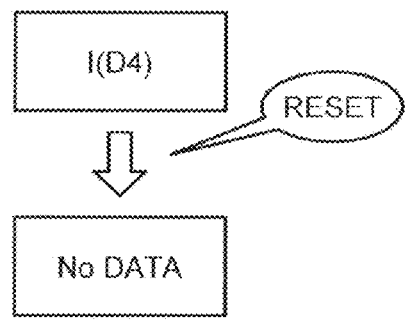
FIG. 9A, FIG. 9B and FIG. 9C are diagrams illustrating an example of a storage process performed by the retention controller according to the first embodiment.
Figure 9B:
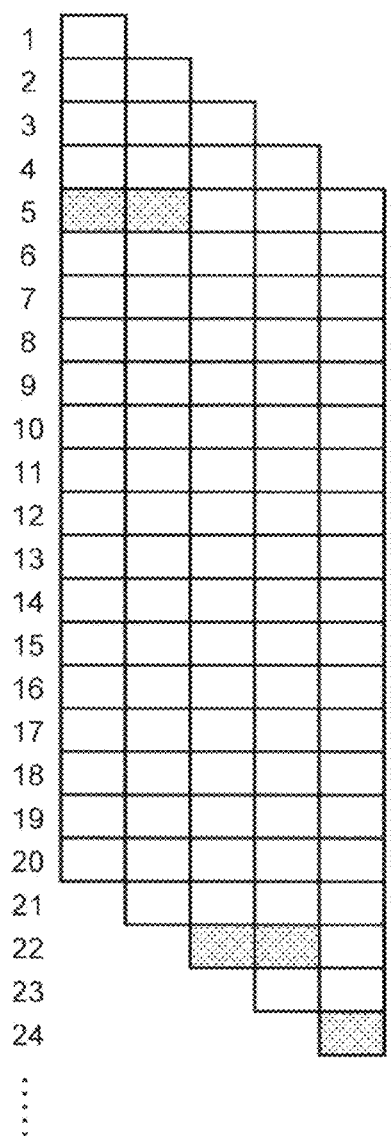
Figure 9C:
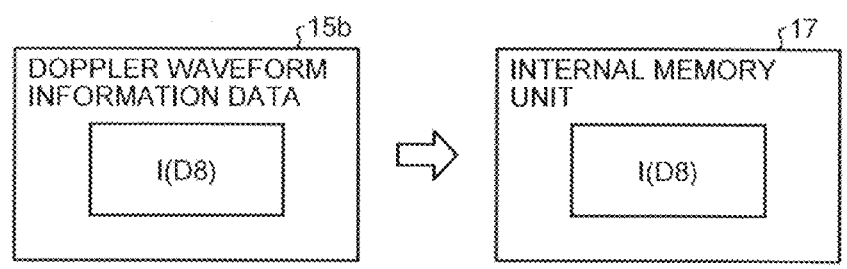

In addition, the retention controller 16c may perform the following processes as well as the above-described updating processes of the maximum waveform information. FIG. 9A, FIG. 9B, and FIG. 9C are diagrams illustrating an example of the reset and storage processes performed by the retention controller according to the first embodiment.

In the process of continuously updating and retaining maximum waveform information according to the present embodiment, maximum waveform information of extreme noise waveforms may be mixed in due to various factors such as body motions or breathing by the subject P, excessive operation of the ultrasonic probe 1, and saturation due to commingling of a valve echo into the echo. Thus, in order to prevent the maximum waveform information of the noise waveforms from being used for the diagnosis, the following reset function is desirably equipped in the retention controller 16c.

When predefined conditions (reset conditions) are satisfied, the retention controller 16c deletes the maximum waveform information from the Doppler waveform information data 15b. Specifically, the retention controller 16c deletes the maximum waveform information when the input device 3 receives a delete request from the operator. For example, the operator refers to image data of "I(D4)" to determine a displayed Doppler waveform is a noise, pressing down a reset button included in the input device 3. This procedure enables the retention controller 16c to delete "I(D4)", which is the maximum waveform information at the present time, point and reset to the state of "No DATA" as illustrated in FIG. 9A.

Alternatively, the retention controller 16c deletes the maximum waveform information every time a predefined period has passed. For example, the retention controller 16c performs the reset process for each preset period (a 30 heart beat period or 30 seconds, for example) in order to prevent the maximum waveform information of noise waveforms from being used for the diagnosis.

Here, when the retention controller 16c performs the reset process, the detector 16a and the determination unit 16b may select Doppler waveforms collected after the reset process as processing targets. However, to update maximum waveform information for the purpose of removing noise waveforms, the detector 16a and the determination unit 16b preferably perform the following processes under the control of the retention controller 16c. Described below with reference to FIG. 9B is an example of processes in which maximum waveform information at the present time point is updated by the retention controller 16c performing the reset process for each period of 20 heart beats.

In the example illustrated in FIG. 9B, it is determined that the maximum value of peak flow velocities is "the peak flow velocity of the fifth heart beat" between the first to the 20th heart beats. Here, the image memory 15 is capable of storing therein peak flow velocities and Doppler waveforms for a 20 heart beat period at most due to its memory capacity limitation. When the peak flow velocity of the Doppler waveform for the 21st heart beat, which is a new heart beat, is input under such a condition, the peak flow velocity for the first heart beat, which is the oldest heart beat, is cleared, and information of "the peak flow velocity for the 5th heart beat", which is the maximum value between the first to the 20th heart beats, is cleared. Then, the determination unit 16b compares the peak flow velocities between the second to the 21st heart beats to determine the maximum value of the peak flow velocities again. In the example illustrated in FIG. 9B, the determination unit 16b determines the maximum value of the peak flow velocities between the second to the 21st flow rates to be "the peak flow rate for the 5th flow rate" again.

Thereafter, when the peak flow velocity of the Doppler waveform for the 22nd heart beat is input, the determination unit 16b determines the maximum value of the peak flow velocities between the third to the 22nd heart beats. In the example illustrated in FIG. 9B, the determination unit 16b determines the maximum value of the peak flow velocities between the third to the 22nd flow rates to be "the peak flow rate for the 22nd flow rate". Thereafter, when the peak flow velocity of the Doppler waveform for the 23rd heart beat is input, the determination unit 16b determines the maximum value of the peak flow velocities between the 4th to the 23rd flow rates. In the example illustrated in FIG. 9B, the determination unit 16b determines the maximum value of the peak flow velocities between the 4th to the 23rd flow rates to be "the peak flow rate for the 22nd flow rate" again. Thereafter, when the peak flow velocity of the Doppler waveform for the 24th heart beat is input, the peak flow velocity of the 4th heart beat is cleared under the control of the retention controller 16c, and the determination unit 16b determines the maximum value of the peak flow velocities between the 5th to the 24th flow rates. In the example illustrated in FIG. 9B, the determination unit 16b determines the maximum value of the peak flow velocities between the 5th to the 24th flow rates to be "the peak flow rate for the 24th flow rate".

With this reset process, the determination unit 16b constantly determines the maximum value of representative flow velocities for the latest set period. The retention controller 16c constantly controls to retain the maximum waveform information corresponding to the maximum value of representative flow velocities for the latest set period. In the example illustrated in FIG. 9B, the determination unit 16b constantly determines the maximum value of peak flow velocities for the last 20 heart beat period. Also, in the example illustrated in FIG. 9B, the retention controller 16c constantly controls to retain the maximum waveform information of the heart beat period in which the maximum value of peak flow velocities in the last 20 heart beat period was detected.

Here, in the present embodiment, the retention controller 16c may use tutorial data of Doppler waveforms to determine if the Doppler waveform retained as the maximum waveform information is a noise waveform and perform the reset process if the Doppler waveform is determined as a noise waveform. In such a case, the determination unit 16b determines the maximum value from the peak flow velocities of the last 20 heart beats with noise waveforms removed.

The processes for preventing maximum waveform information of a noise waveform from being used should not be limited to the reset process and the retention controller 16c may perform the following retention control process. If the operator determines a Doppler waveform to be a noise waveform and presses down the reset button, or if the retention controller 16c determines a Doppler waveform to be a noise waveform, the retention controller 16c controls to maintain the maximum waveform information that was retained immediately before the noise waveform in question.

Furthermore, in the present embodiment, if a request to store maximum waveform information is received from the operator, the retention controller 16c outputs the maximum waveform information in question in a predefined format (file) into a predefined storage medium. For example, the retention controller 16c converts image data of maximum waveform information specified by the operator into the JPEG (Joint Photographic Experts Group) format to be output into a predefined storage medium and converts a measured value of the maximum waveform information into the CSV (Comma Separated Values) format to be output into a predefined storage medium. For example, if the "Storage button" included in the input device 3 is pressed down, the retention controller 16c controls the internal memory unit 17 to store therein "I(D8)" retained in the Doppler waveform information data 15b as illustrated in FIG. 9C. Alternatively, the retention controller 16c controls maximum waveform information retained in the Doppler waveform information data 15b to be output and stored in a portable storage medium. Alternatively, the retention controller 16c may control data specified by the operator (image data, all measured values, part of the measured values, for example) out of the maximum waveform information retained by the Doppler waveform information data 15b to be output and stored. It should be noted that the retention controller 16c may output the maximum waveform information retained in the Doppler waveform information data 15b to an external device such as a printer.

Here, in the state that the display illustrated in the lower diagram in FIG. 8 is presented, the operator may manually trace the envelope of the Doppler waveform displayed in the maximum waveform display area 102 to control the detector 16a to measure various measured values again as necessary after pressing down the "Freeze button". However, the operator may want to determine if a Doppler waveform of maximum waveform information is a waveform collected with peak flow velocities in a relatively stable state or a waveform collected with peak flow velocities transiently rising. In addition, it is inconvenient for the operator to manually scroll the collected images back to the past at the time of measurement or storage as in the conventional operation. Accordingly, the display controller 16d according to the present embodiment may perform the following display control.

Figure 10:
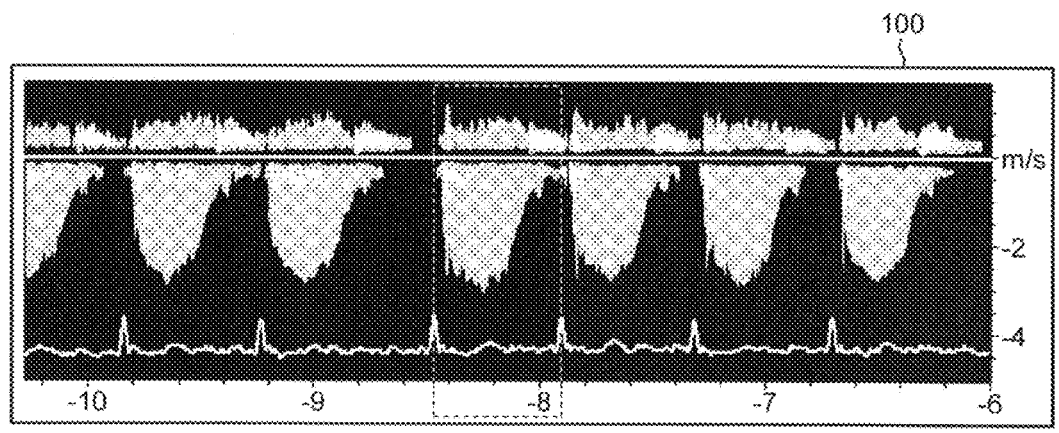
FIG. 10 is a diagram illustrating an example of a scroll process performed by the display controller according to the first embodiment.

When the display controller 16d receives a request to display maximum waveform information from the operator, the display controller 16d controls the monitor 2 to display continuous Doppler waveforms including the Doppler waveform corresponding to the maximum waveform information in question. Specifically, when the display controller 16d receives a request to display maximum waveform information from the operator, the display controller 16d controls the monitor 2 to display continuous Doppler waveforms for a period of one or more heart beats including the Doppler waveform corresponding to the maximum waveform information in question. In other words, the display controller 16d automatically performs a scroll process that has been manually performed in conventional cases. For example, if the operator who has pressed down the "Freeze button" further specifies the maximum waveform display area 102 or the measured value display area 103 with a mouse or the like, the display controller 16d controls the monitor 2 to display a group of Doppler waveforms for a period of continuous heart beats centering on the Doppler waveform of the maximum waveform information from the collection waveform data 15a. Alternatively, at the time point when the "Freeze button" is pressed down, the display controller 16d controls the monitor 2 to display a group of Doppler waveforms for a period of continuous heart beats centering on the Doppler waveform of the maximum waveform information from the collection waveform data 15a, for example. FIG. 10 is a diagram illustrating an example of the scroll process performed by the display controller according to the first embodiment.

For example, the display controller 16d recovers the display area to the state illustrated in the upper diagram of FIG. 8 and controls the waveform display area 100 to display a group of Doppler waveforms for a period of about 6.5 heart beats centering on the Doppler waveform of the maximum waveform information as illustrated in FIG. 10. The example in FIG. 10 illustrates a group of Doppler waveforms for a period of about 6.5 heart beats centering on the Doppler waveform at about 8 seconds before the time when the "Freeze button" is pressed down. Because the waveform display area 100 displays continuous Doppler waveforms for about 4.2 seconds due to the display scales, the display controller 16d performs an automatic scroll process returning to the past for about 4 seconds in the example illustrated in FIG. 10.

The operator refers to the Doppler waveforms illustrated in FIG. 10 to perform a remeasurement process and make a storage request. It should be noted that if a storage request is made in the state illustrated in FIG. 10, both the case where, as maximum waveform information, image data of the maximum waveform information in question is stored and the case where, as maximum waveform information, image data of all Doppler waveforms illustrated in FIG. 10 are stored are acceptable.

Figure 11:
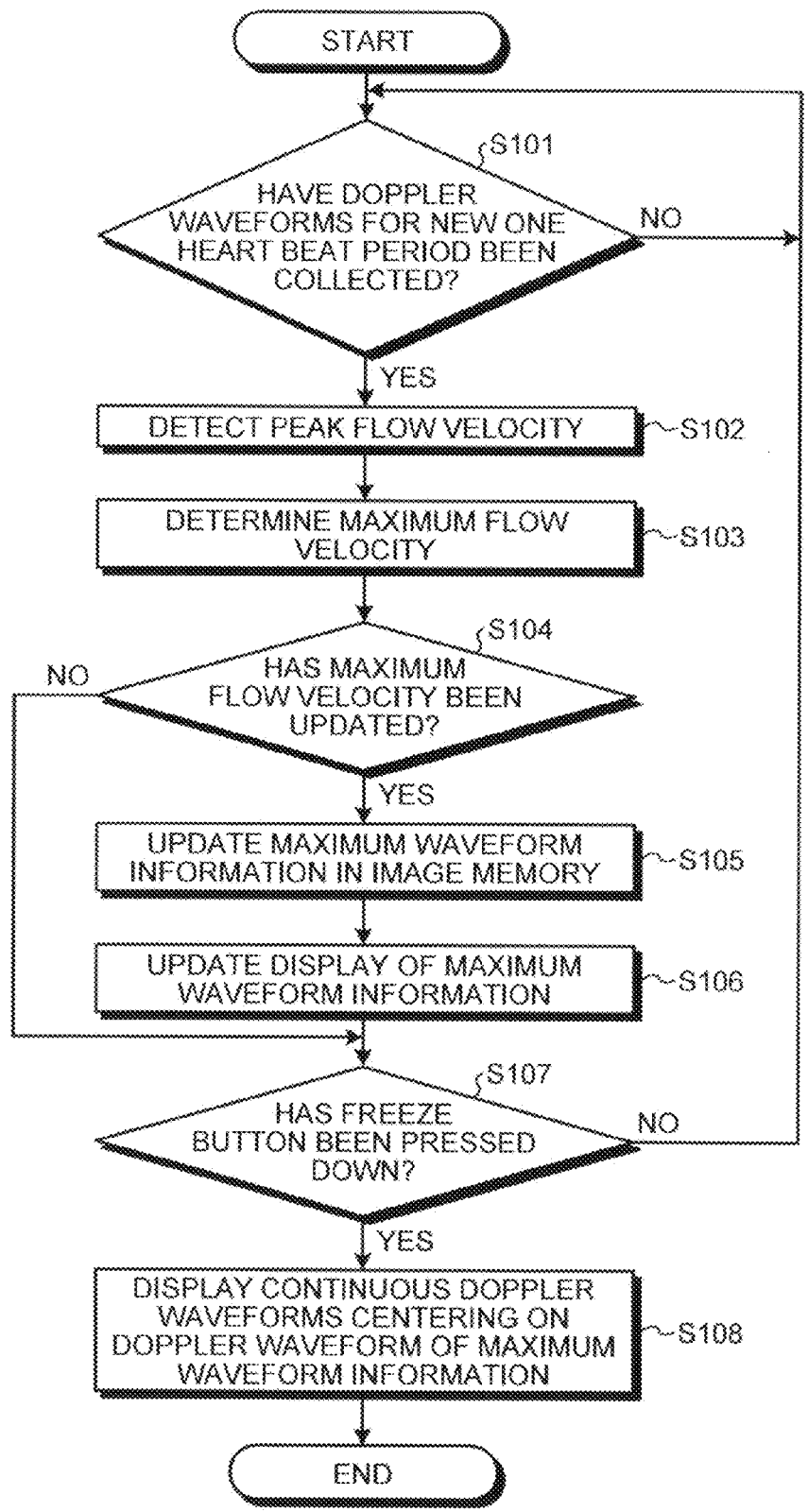
FIG. 11 is a flowchart illustrating retention and display processes of maximum waveform information performed by the ultrasound diagnosis apparatus according to the first embodiment.
Figure 12:
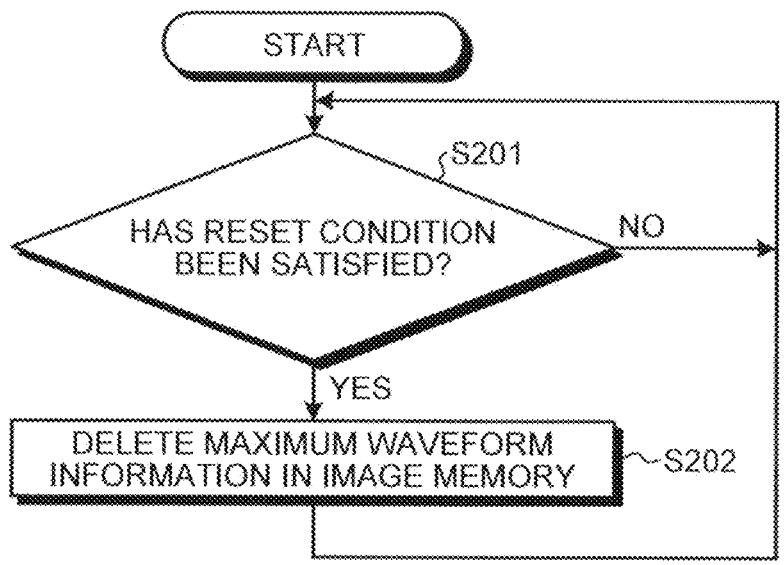
FIG. 12 is a flowchart illustrating a reset process performed by the ultrasound diagnosis apparatus according to the first embodiment.
Figure 13:
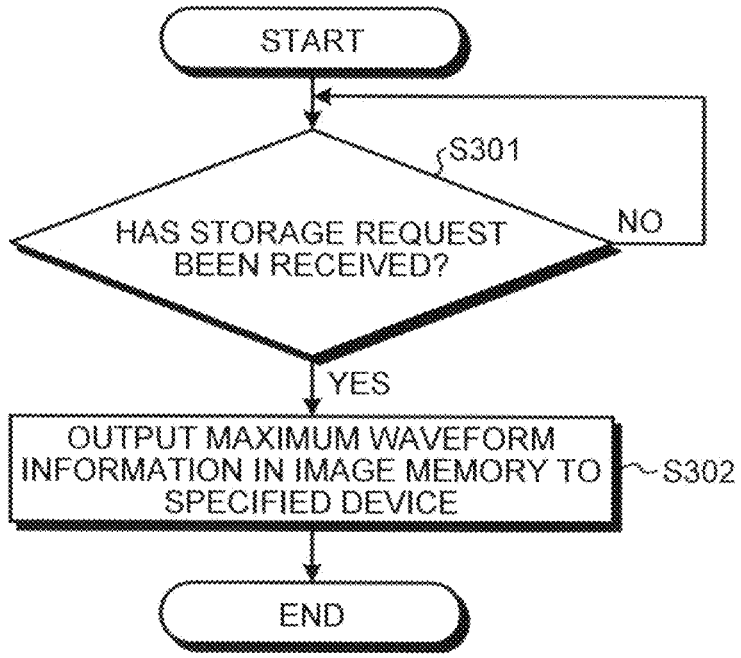
FIG. 13 is a flowchart illustrating a storage process performed by the ultrasound diagnosis apparatus according to the first embodiment.

Next, with reference to FIG. 11, FIG. 12, and FIG. 13, processes performed by the ultrasound diagnostic apparatus according to the first embodiment are described. FIG. 11 is a flowchart illustrating retention and display processes of maximum waveform information performed by the ultrasound diagnosis apparatus according to the first embodiment. FIG. 12 is a flowchart illustrating a reset process performed by the ultrasound diagnosis apparatus according to the first embodiment. FIG. 13 is a flowchart illustrating a storage process performed by the ultrasound diagnosis apparatus according to the first embodiment.

In retention and display processes of maximum waveform information, the detector 16a of the ultrasound diagnostic apparatus according to the first embodiment determines if a Doppler waveform of a period of a new heart beat has been collected as illustrated in FIG. 11 (Step S101). If a Doppler waveform for a period of a new heart beat has not been collected (No at Step S101), the detector 16a waits until a Doppler waveform for a period of a new heart beat is collected.

If a Doppler waveform for a period of a new heart beat has been collected (Yes at Step S101), the detector 16a detects a peak flow rate of the Doppler waveform in question using an envelope detection function (Step S102). The determination unit 16b determines the maximum flow velocity at the present time point (Step S103).

The retention controller 16c determines if a maximum flow velocity has been updated (Step S104). If the maximum flow velocity has been updated (Yes at Step S104), the detector 16a calculates a measured value from the Doppler waveform of which a new maximum flow velocity is detected, and the retention controller 16c updates maximum waveform information in the image memory 15 (Step S105). The display controller 16d updates display of the maximum waveform information (Step S106).

After the process of Step S106 or if the maximum waveform information value is not updated in the determination process at Step S104 (No at Step S104), the display controller 16d determines if the Freeze button has been pressed down (Step S107). If the Freeze button has not been pressed down (No at Step S107), the detector 16a returns to Step S101 and determines if a Doppler waveform for a period of a new heart beat has been collected.

If the Freeze button has been pressed down (Yes at Step S107), the display controller 16d controls to display continuous Doppler waveforms centering on the Doppler waveform of the maximum waveform information (Step S108), completing the process. It should be noted that the automatic scroll process at Step S108 may be performed if the maximum waveform display area 102 or the measured value display area 103 is specified after the Freeze button was pressed down.

In the reset process, the retention controller 16c of the ultrasound diagnostic apparatus according to the first embodiment determines if the reset condition is satisfied as illustrated in FIG. 12 (Step S201). If the reset condition is not satisfied (No at Step S201), the retention controller 16c waits until the reset condition is satisfied.

If the reset condition is satisfied (Yes at Step S201), the retention controller 16c deletes maximum waveform information in the image memory 15 (Step S202) and performs the control process exemplified in FIG. 9B, storing updated maximum waveform information. Thereafter, the retention controller 16c performs the determination process at Step S201. It should be noted that the retention controller 16c completes the reset process if the Freeze button is pressed down, for example.

In the storage process, the retention controller 16c of the ultrasound diagnostic apparatus according to the first embodiment determines if a storage request has been received from the operator as illustrated in FIG. 13 (Step S301). If a storage request has not been received (No at Step S301), the retention controller 16c waits until a storage request is received.

If a storage request has been received (Yes at Step S301), the retention controller 16c outputs maximum waveform information in the image memory 15 (Step S302) and completes the process.

As described above, because maximum waveform information is displayed in the maximum waveform display area 102 and the measured value display area 103 in a constantly updated manner in the first embodiment, the operator can grasp the maximum waveform information without depending on his or her memory while changing the way of putting the ultrasonic prove 1 or verbally controlling breathing of the subject P. In addition, the recording period of a Doppler waveform is set to 10 seconds, for example, in conventional cases. In other words, Doppler waveforms retained in the collection waveform data 15a in the image memory 15 are Doppler waveforms for the preset recording period. However, because the control by the retention controller 16c ensures the maximum waveform information to be retained in the Doppler waveform information data 15b, the operator can avoid missing the maximum waveform information and performing a retest. Accordingly, in the first embodiment, it is possible to alleviate the burden on the operator collecting Doppler waveforms with the maximum peak flow velocity.

Furthermore, the first embodiment can alleviate the burden on the operator performing measurement processes by tracing the boundaries of Doppler waveforms through known automatic tracing. The first embodiment also enables the operator to select a measured value of maximum waveform information as necessary. After pressing down the "Freeze button", the operator can also manually trace the envelope of a Doppler waveform displayed on the maximum waveform display area 102 to control the detector 16a to perform remeasurement of various values.

Furthermore, in the first embodiment, performing the reset process can prevent noise waveforms from being used for diagnosis of severity of a cardiac valve. The first embodiment also enables the operator to perform the storage process of maximum waveform information in a simple manner. In addition, the first embodiment enables the automatic scroll process, thereby alleviating the burden on the operator.

Furthermore, in the first embodiment, the maximum waveform display area 102 and the latest waveform display area 101 are displayed in parallel at the same scale. Because the scales for image data displayed in the maximum waveform display area 102 and image data displayed in the latest waveform display area 101 are the same, the operator can easily compare peak flow velocities of Doppler waveforms of maximum waveform information and peak flow velocities of Doppler waveforms displayed in the latest waveform display area 101.

It should be noted that display of measured values of maximum waveform information is not always necessary because the operator can grasp the Doppler waveform of which the peak flow velocity is the maximum value by referring to image data of the maximum waveform information. Even in a case where only the image data of the maximum waveform information is displayed, the operator can easily estimate peak flow velocities through the use of the same scale for both the maximum waveform display area 102 and the latest waveform display area 101 as described above, improving the level of reliability of the estimated value obtained through observation of crest values.

Figure 14:
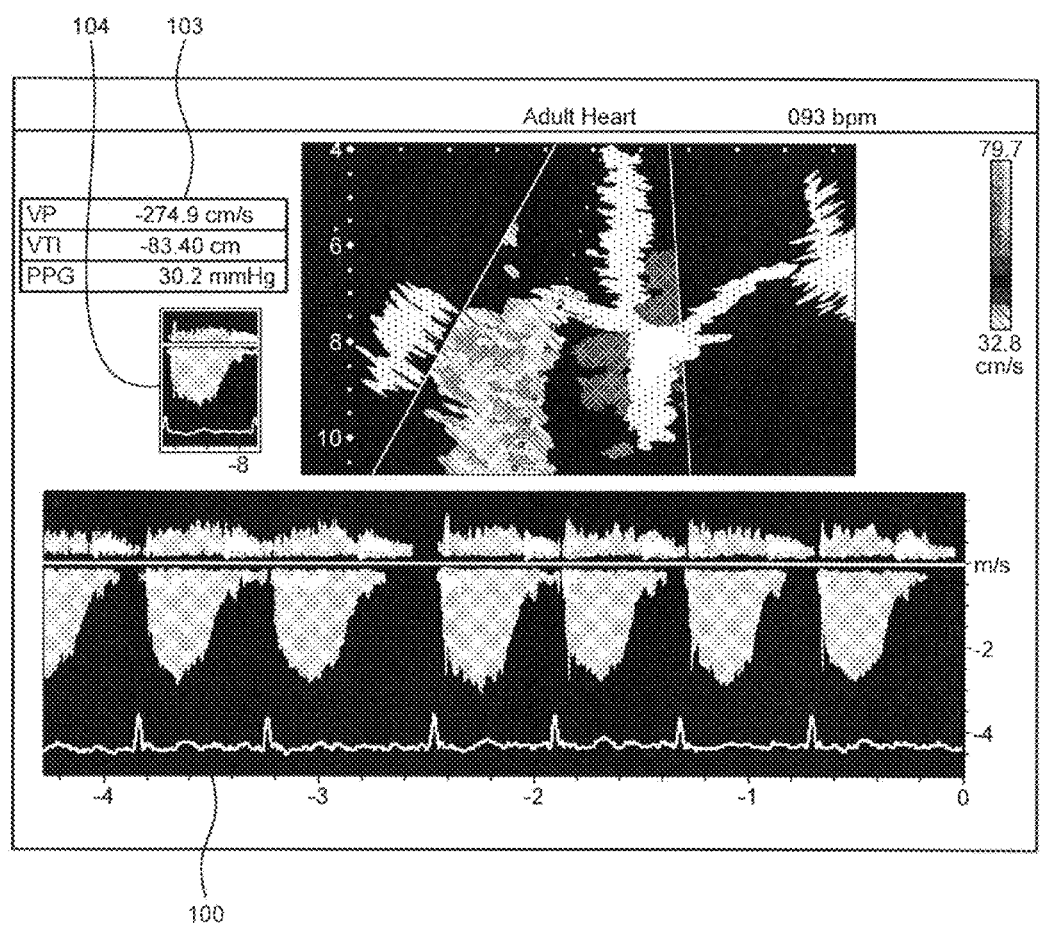
FIG. 14 is a diagram illustrating an example of a display process performed by a display controller according to a second embodiment.

In a second embodiment, described with reference to FIG. 14 is a case where maximum waveform information is displayed in a form different from the first embodiment. FIG. 14 is a diagram illustrating an example of a display process performed by a display controller according to the second embodiment. It should be noted that the present embodiment will also be described on the premise that the predefined period is a one heart beat period.

The display controller 16d according to the second embodiment makes the display scale for image data of the Doppler waveforms corresponding to maximum waveform information different from the display scale for image data of the Doppler waveforms collected by the present time point. In the first embodiment, image data of maximum waveform information is displayed in parallel at the same display scale as that of image data of the Doppler waveforms that have been collected by the present time point as illustrated in the lower diagram in FIG. 8. In such a case, the display area of Live Doppler waveforms will be narrowed down from the waveform display area 100 to the latest waveform display area 101. To address this in the second embodiment, the display controller 16d maintains the display area of the Live Doppler waveform in the waveform display area 100 and sets a thumbnail display area 104 that is the maximum waveform display area 102 scaled down in size above the waveform display area 100 as illustrated in FIG. 14. In other words, the display controller 16d according to the second embodiment controls the thumbnail display area 104 to display scale-down image data of the Doppler waveforms of maximum waveform information. It should be noted that in the example illustrated in FIG. 14, the display controller 16d sets the measured value display area 103 above the thumbnail display area 104.

In the second embodiment, it is possible to display image data of Doppler waveforms of maximum waveform information with a display area for the Live Doppler waveform secured. Furthermore, by setting the thumbnail display area 104 in a position apart from the waveform display area 100, the display position of the Doppler waveforms of the maximum waveform information becomes clear for the operator. It should be noted that if the monitor 2 has enough space for display, the display controller 16d may display enlarged image data of the Doppler waveforms of the maximum waveform information. Enlargement is useful when the operator wants to observe the Doppler waveforms of the maximum waveform information in detail.

The reset, storage, and scroll processes described in the first embodiment are applicable to the second embodiment as well. For example, the control unit 16 according to the second embodiment is able to perform the storage and scroll processes when the operator specifies the thumbnail display area 104. Furthermore, also in the second embodiment, control may be performed so that the manual or automatic noise determination process described in the first embodiment is performed, thereby not retaining Doppler waveform information of a noise waveform but maintaining maximum waveform information retained immediately before the noise waveform in question. Furthermore, because the second embodiment can also enable the operator to grasp a Doppler waveform of which the peak flow velocity is the maximum by referring to image data of maximum waveform information, display of measured values of the maximum waveform information is not always necessary. In addition, also in the second embodiment, when Doppler waveforms are collected through the PW method, a representative flow velocity detected by the detector 16a will be a peak flow velocity or an average flow velocity.

Figure 15:
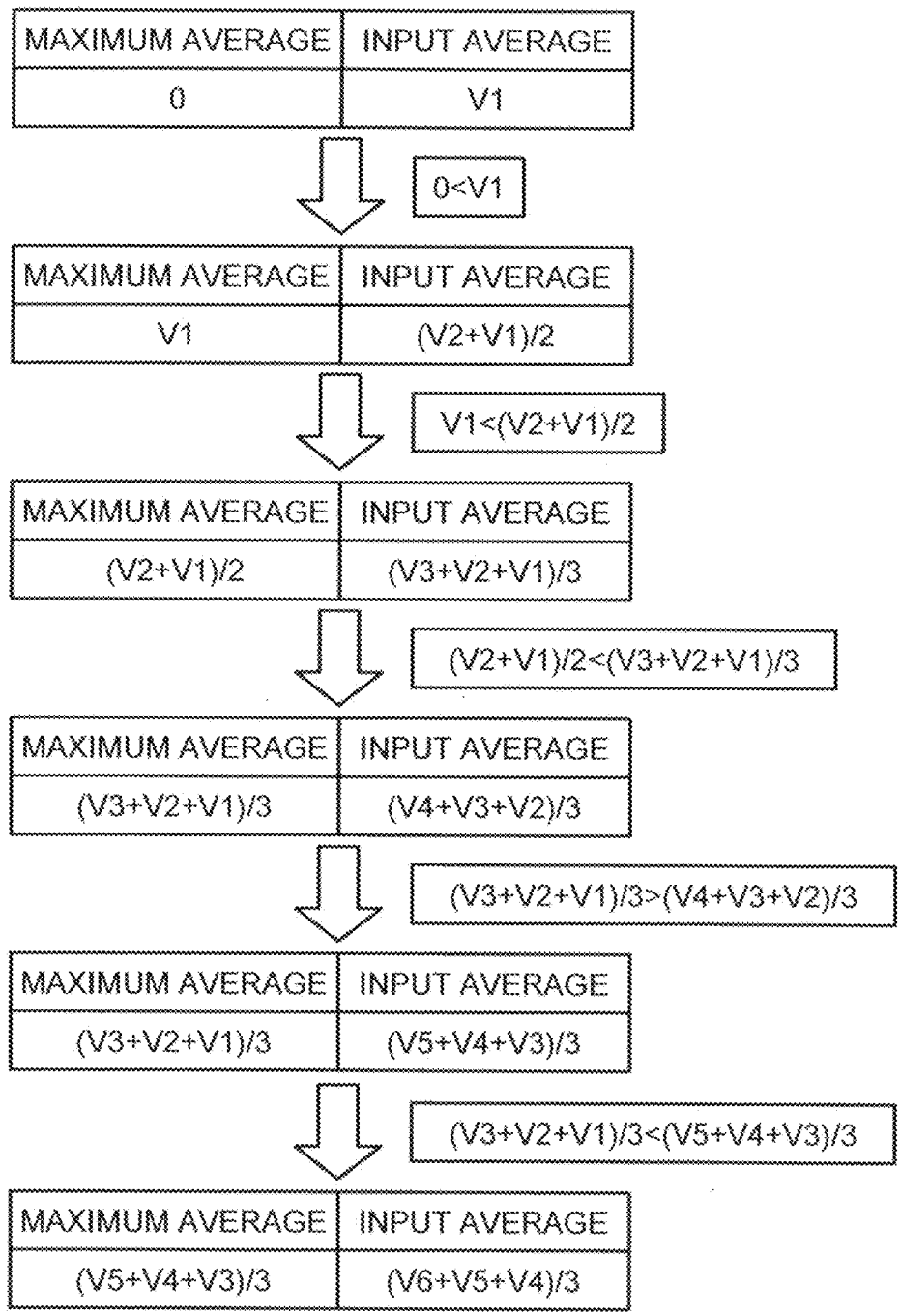
FIG. 15 and FIG. 16 are diagrams illustrating a third embodiment.
Figure 16:
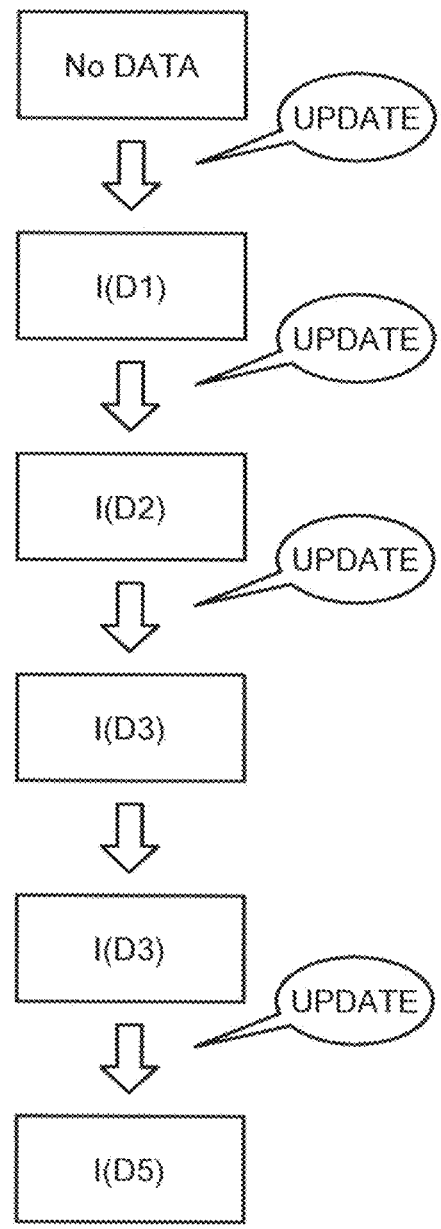

In a third embodiment, described with reference to FIG. 15 and FIG. 16 is a case where using an average of peak flow velocities for a period of a plurality of heart beats. FIG. 15 and FIG. 16 are diagrams illustrating the third embodiment. It should be noted that the present embodiment is also described on the premise that the predefined period is a one heart beat period.

The detector 16a according to the third embodiment calculates an average of representative flow velocities of Doppler waveforms for the latest predefined period and representative flow velocities of Doppler waveforms for at least one predefined period that were collected immediately before the latest Doppler waveforms in question. In the present embodiment, the detector 16a calculates an average of peak flow velocities. In other words, the detector 16a calculates an average of peak flow velocities of Doppler waveforms for a period of the latest heart beat and peak flow velocities of Doppler waveforms for at least a period of one heart beat that were collected immediately before the latest Doppler waveforms in question. The determination unit 16b according to the third embodiment compares the averages sequentially output from the detector 16a, thereby determining the maximum average at the present time point (hereinafter, described as the maximum average).

Specifically, in the third embodiment, an average of peak flow velocities in the past continuous three to five heart beats including the present heart beat is used. Described below is a case where "3" is set to the number of continuous heart beats. Also, the description below is on the premise that Doppler waveforms "D1 to D6" are sequentially detected and the detector 16a sequentially detects peak flow velocities "V1 to V6" of each of the Doppler waveforms. In addition, until three Doppler waveforms are collected, the detector 16a outputs "V1" and "(V2+V1)/2" to the determination unit 16b as averages. If three or more of the Doppler waveforms are collected, the detector 16a sequentially outputs "(V3+V2+V1)/3", "(V4+V3+V2)/3", "(V5+V4+V3)/3", and "(V6+V5+V4)/3" to the determination unit 16b. Furthermore, the determination unit 16b uses absolute values of the values received from the detector 16a in the present embodiment.

As illustrated in FIG. 15, the determination unit 16b sets an initial value for the maximum average to "0", and compares the initial value "0" and "V1" that is a first average (input average) received from the detector 16a. Next, the determination unit 16b updates the maximum average to "V1" because "0<V1" as illustrated in FIG. 15. Thereafter, the determination unit 16b compares "input average: (V2+V1)/2" and "maximum average: V1", and updates the maximum average to "(V2+V1)/2" because "V1<(V2+V1)/2" as illustrated in FIG. 15.

Furthermore, the determination unit 16b compares "input average: (V3+V2+V1)/3" and "maximum average: (V2+V1)/2", and updates the maximum average to "(V3+V2+V1)/3" because "(V2+V1)/2<(V3+V2+V1)/3" as illustrated in FIG. 15. Thereafter, the determination unit 16b compares "input average: (V4+V3+V2)/3" and "maximum average: (V3+V2+V1)/3", and maintains the maximum average as "(V3+V2+V1)/3" without updating because "(V3+V2+V1)/3>(V4+V3+V2)/3" as illustrated in FIG. 15.

Furthermore, the determination unit 16b compares "input average: (V5+V4+V3)/3" and "maximum average: (V3+V2+V1)/3", and updates the maximum average to "(V5+V4+V3)/3" because "(V3+V2+V1)/3<(V5+V4+V3)/3" as illustrated in FIG. 15. Thereafter, the determination unit 16b compares "input average: (V6+V5+V4)/3" and "maximum average: (V5+V4+V3)/3".

By sequentially performing the comparison process using averages illustrated in FIG. 15, the determination unit 16b determines the maximum average at the present time point. It should be noted that the detector 16a may average out Doppler waveforms for a period of the latest heart beat and Doppler waveforms for at least a period of a heart beat that were collected immediately before the latest Doppler waveforms in question, and output a representative flow velocity detected with a waveform thus averaged as an average of the above-described values to the determination unit 16b.

Furthermore, the retention controller 16c according to the third embodiment controls to retain Doppler waveform information of Doppler waveforms for the latest predefined period out of Doppler waveforms for a plurality of predefined periods in which the maximum averages were detected as maximum waveform information in the Doppler waveform information data 15b in the image memory 15. Specifically, the retention controller 16c controls to retain Doppler waveform information of the Doppler waveforms for a period of the latest heart beat out of Doppler waveforms for a period of a plurality of heart beats in which the maximum averages were detected as maximum waveform information in the Doppler waveform information data 15b in the image memory 15.

The example illustrated in FIG. 16 indicates a process performed by the retention controller 16c based on the results of the processes performed by the determination 16b illustrated in FIG. 15. It should be noted that in FIG. 16, maximum waveform information is presented as "I(D3)" in a case where the latest Doppler waveform is "D3" out of the three Doppler waveforms in which the maximum averages were detected.

First, from the start of the Doppler waveform collection until the time point at which Doppler waveforms for a one heart beat period have not been collected, the Doppler waveform information data 15b is in a "No DATA" state as illustrated in FIG. 16. Next, if the maximum flow velocity is updated to "V1", the retention controller 16c updates data to be retained by the Doppler waveform information data 15b from "No DATA" to "I(D1)" as illustrated in FIG. 16. Next, if the maximum flow velocity is updated to "(V2+V1)/2", the retention controller 16c updates data to be retained by the Doppler waveform information data 15b from "I(D1)" to ["I(D2)" that is waveform information of a Doppler waveform D2 for which "V2" was measured] as illustrated in FIG. 16.

Next, if the maximum flow velocity is updated to "(V3+V2+V1)/3", the retention controller 16c updates data to be retained by the Doppler waveform information data 15b from "I(D2)" to ["I(D3)" that is waveform information of a Doppler waveform D3 for which "V3" was measured] as illustrated in FIG. 16. Next, if the maximum average is not updated from "(V3+V2+V1)/3", the retention controller 16c maintains data to be retained by the Doppler waveform information data 15b as "I(D3)" as illustrated in FIG. 16.

Next, if the maximum flow velocity is updated to "(V5+V4+V3)/3", the retention controller 16c updates data to be retained by the Doppler waveform information data 15b from "I(D3)" to ["I(D5)" that is waveform information of a Doppler waveform D5 for which "V5" was measured] as illustrated in FIG. 16.

The display controller 16d displays maximum waveform information in a sequentially updated manner in the display form described in the first embodiment or in the display form described in the second embodiment.

As described above, the processes described in the first embodiment and the second embodiment are processes of retaining peak flow velocities determined by the unit of one heart beat. In contrast, in the third embodiment, retention processes are performed using averages of peak flow velocities by the unit of a plurality of heart beats. Processes in the third embodiment are effective in a case where diagnosis is desired to be performed using relatively stable peak values or Doppler waveforms for which relatively stable peak values continue for a plurality of heart beats, not transient peak values. It should be noted that also in the third embodiment, when Doppler waveforms are collected through the PW method, a representative flow velocity detected by the detector 16a will be a peak flow velocity or an average flow velocity. In addition, the reset process described with reference to FIG. 9B is applicable to the third embodiment as well. For example, the determination unit 16b constantly determines the maximum average for the last 20 heart beat period under the control of the retention controller 16c.

Figure 17A:
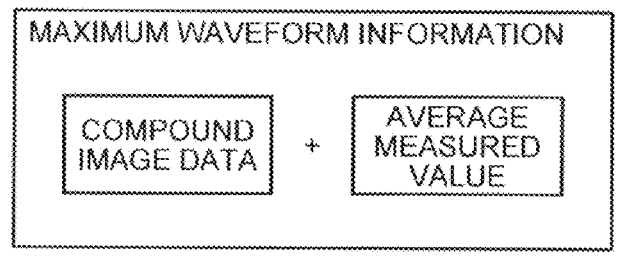
FIG. 17A and FIG. 17B are diagrams illustrating a fourth embodiment.
Figure 17B:
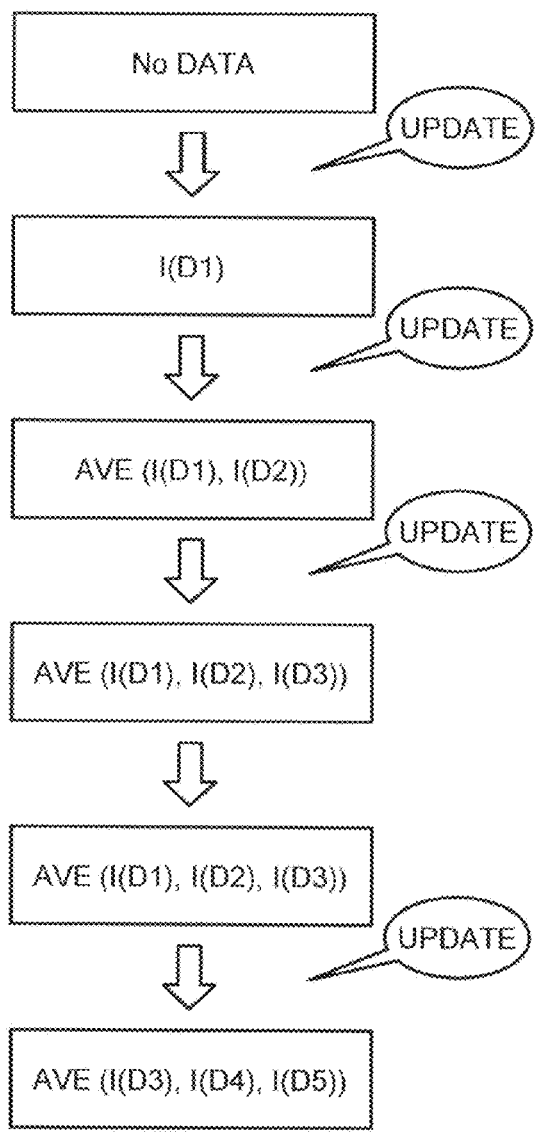

In a fourth embodiment, described with reference to FIG. 17A and FIG. 17B is a case where maximum waveform information is retained in a form different from the third embodiment. FIG. 17A and FIG. 17B are diagrams illustrating the fourth embodiment. It should be noted that the present embodiment is also described on the premise that the predefined period is a one heart beat period.

In the third embodiment in which maximum waveform information is updated using an average of peak flow velocities for continuous heart beats, there is a case where even a measured value is desired to be displayed by an average measure value. In such a case, "(V3+V2+V1)/3" is displayed instead of "maximum flow velocity: V3" and image data of "D3" is displayed, for example.

If "(V3+V2+V1)/3" and "D3" are displayed as maximum waveform information, the operator will feel wrong. In other words, the operator will not be able to confirm "(V3+V2+V1)/3" as an estimate even if referring to "D3".

Thus, the retention controller 16c according to the fourth embodiment controls to retain average waveform information that is the average of Doppler waveforms for a plurality of predefined periods in which the maximum average was calculated as maximum waveform information in the Doppler waveform information data 15b in the image memory 15. Specifically, the retention controller 16c controls to retain average waveform information that is the average of Doppler waveforms for a plurality of heart beats in which the maximum average was calculated as maximum waveform information in the Doppler waveform information data 15b in the image memory 15.

As illustrated in FIG. 17A, the retention controller 16c according to the fourth embodiment sets a measured value of maximum waveform information to an average (average measured value) of various measured values that have been measured from each Doppler waveform for a plurality of heart beats in which the maximum average was calculated. For example, if "(V3+V2+V1)/3" is the maximum average and a PPG is specified as a measured value, the retention controller 16c controls the image memory 15 to retain the average of a PPG measured from D1, a PPG measured from D2, and a PPG measured from D3 as a measured value of maximum waveform information.

Furthermore, the retention controller 16c according to the fourth embodiment controls the image generating unit 14 to generate compounded (median or arithmetic mean) image data of Doppler waveforms for a plurality of heart beats in which the maximum average was calculated. Thereafter, the retention controller 16c according to the fourth embodiment controls the image memory 15 to retain the compound image data as image data of maximum waveform information.

The example illustrated in FIG. 17B indicates processes performed by the retention controller 16c according to the fourth embodiment based on the results from the determination unit 16b illustrated in FIG. 15. It should be noted that in FIG. 17B, average waveform information in a case where the three Doppler waveforms from which the maximum averages were detected were "D1, D2, and D3" are indicated as "AVE (I(D1), I(D2), I(D3))".

First, from the start of the Doppler waveform collection until the time point at which Doppler waveforms for a one heart beat period have not been collected, the Doppler waveform information data 15b is in a "No DATA" state as illustrated in FIG. 17B. Next, if the maximum average is updated to "V1", the retention controller 16c updates data to be retained by the Doppler waveform information data 15b from "No DATA" to "I(D1)" as illustrated in FIG. 17B. Next, if the maximum average is updated to "(V2+V1)/2", the retention controller 16c updates the data to be retained by the Doppler waveform information data 15b from "I(D1)" to "AVE(I(D1), I(D2))" as illustrated in FIG. 17B.

Next, if the maximum average is updated to "(V3+V2+V1)/3", the retention controller 16c updates data to be retained by the Doppler waveform information data 15b from "AVE(I(D1), I(D2))" to "AVE(I(D1), I(D2), I(D3))" as illustrated in FIG. 17B. Next, if the maximum flow velocity maximum average is not updated from "(V3+V2+V1)/3", the retention controller 16c maintains the data to be retained by the Doppler waveform information data 15b of "AVE(I(D1), I(D2), I(D3))" as illustrated in FIG. 17B.

Next, if the maximum average is updated to "(V5+V4+V3)/3", the retention controller 16c updates the data to be retained by the Doppler waveform information data 15b from "AVE(I(D1), I(D2), I(D3))" to "AVE(I(D3), I(D4), I(D5))" as illustrated in FIG. 17B.

Furthermore, the display controller 16d controls to display the maximum waveform information that is the average waveform information in a sequentially updated manner in the display form described in the first embodiment or in the display form described in the second embodiment.

In the fourth embodiment, the average waveform information is held and displayed. Therefore, the fourth embodiment is suitable for a case where it is desirable to observe heart beats in a relatively long period and to obtain average maximum flow velocities and the information of Doppler waveforms for which the average maximum flow velocities are measured. It should be noted that the reset, storage, and scroll processes described in the first embodiment are applicable to the third and the fourth embodiments as well. Furthermore, also in the third and the fourth embodiments, control may be performed so that the manual or automatic noise determination process described in the first embodiment is performed, thereby not retaining Doppler waveform information of a noise waveform but maintaining maximum waveform information retained immediately before the noise waveform in question. In addition, also in the fourth embodiment, when Doppler waveforms are collected through the PW method, a representative flow velocity detected by the detector 16a will be a peak flow velocity or an average flow velocity.

In the first to the fourth embodiment, cases where one piece of Doppler waveform information is retained in the Doppler waveform information data 15b. In a fifth embodiment, described with reference to FIG. 18A, FIG. 18B, and FIGS. 19 to 22 is a case where a plurality of pieces of Doppler waveform information are retained in the Doppler waveform information data 15b. FIG. 18A, FIG. 18B, and FIGS. 19 to 22 are diagrams illustrating the fifth embodiment. It should be noted that also in the present embodiment, description is made on the premise that the predefined period is a one heart beat period.

In other words, the retention controller 16c according to the fifth embodiment controls to retain Doppler waveforms for at least a one heart beat period with maximum waveform information in the Doppler waveform information data 15b. Specifically, the retention controller 16c controls to retain Doppler waveform information for at least a one heart beat period with the maximum waveform information in the Doppler waveform information data 15b. Furthermore, the display controller 16d according to the fifth embodiment controls the monitor 2 to display a plurality of pieces of Doppler waveform information retained in the Doppler waveform information data 15b.

Described below are patterns of pieces of the Doppler waveform information retained in the Doppler waveform information data 15b. The patterns are divided into a first pattern and a second pattern, and the description is made sequentially for each pattern. It should be noted that the description below is made for a case where three pieces of Doppler waveform information are retained in the Doppler waveform information data 15b as an example.

Figure 18A:
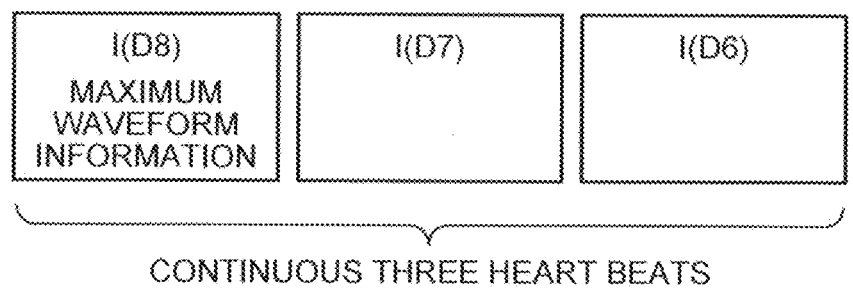
FIG. 18A, FIG. 18B, FIG. 19, FIG. 20, FIG. 21, and FIG. 22 are diagrams illustrating a fifth embodiment.

In the first pattern, the retention controller 16c controls to retain Doppler waveform information for a plurality of continuous predefined periods including maximum waveform information in the Doppler waveform information data 15b. Specifically, the retention controller 16c controls to retain Doppler waveform information for continuous heart beats including maximum waveform information in the Doppler waveform information data 15b. For example, as illustrated in FIG. 18A, if the retention controller 16c controls to retain maximum waveform information "I(D8)" of a Doppler waveform "D8" that is the maximum flow velocity at the present time point, the retention controller 16c controls to retain "I(D7)" and "I(D6)", each of which is Doppler waveform information of two Doppler waveforms collected before the Doppler waveform "D8". "I(D7)" is Doppler waveform information of "D7", which is a Doppler waveform for a one heart beat period collected immediately before the Doppler waveform "D8", and "I(D6)" is Doppler waveform information of "D6", which is a Doppler waveform for a one heart beat period collected immediately before the Doppler waveform "D7".

Figure 18B:
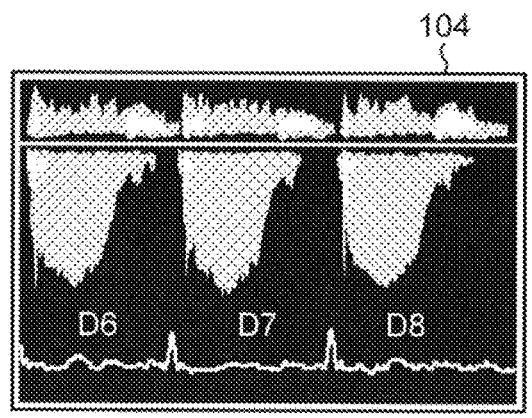

In the first pattern, the display controller 16d controls to display the thumbnail display area 104 to display "D6, D7, and D8" as illustrated in FIG. 18B, for example. It should be noted that with respect to measured values, both a case where the display controller 16d controls to display only measured values included in "I(D8)" and a case where the display controller 16d controls to display measured values included in "I(D7)" and "I(D6)" as well as the measured values included in "I(D8)".

In the first pattern, the operator can determine if he or she should press down the "Freeze button" while acquiring information of Doppler waveforms for continuous three heart beats by referring to "D6, D7, and D8", for example. Furthermore, the operator can observe "D6, D7, and D8" again in detail after pressing down the "Freeze button". For example, if the operator has determined that a value of a peak flow velocity is rather low compared with "D8" but the waveform "D6" does not include a noise, the operator can perform remeasurement using "D6". In such a case, the operator can make a storage request of "D6", not "D8".

Furthermore, in the first pattern, even if only "D1 to D5" are stored in the collection waveform data 15a, scroll display is possible. For example, if a scroll display request is made by specifying "D8", it is possible for the display controller 16d to read at least "D6, D7, and D8" from the Doppler waveform information data 15b and perform scroll display. It should be noted that also in the first pattern, it is possible to perform the reset process described in the first embodiment. Furthermore, also in the first pattern, control may be performed so that the manual or automatic noise determination process described in the first embodiment is performed, thereby not retaining Doppler waveform information of a noise waveform but maintaining a plurality of Doppler waveform information retained immediately before the noise waveform in question.

Figure 19:
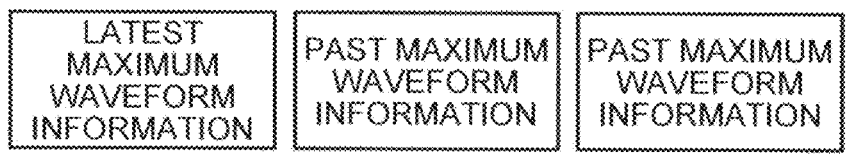

Next, in the second pattern, the retention controller 16c controls to retain maximum waveform information in the Doppler waveform information data 15b at the same time controlling to maintain at least a piece of past maximum waveform information that is a piece of Doppler waveform information having been a piece of maximum waveform information before the maximum waveform information in question and to retain the past maximum waveform information thus maintained in the Doppler waveform information data 15b. For example, in the second pattern, the retention controller 16c controls to retain maximum waveform information at the present time point (latest maximum waveform information) as illustrated in FIG. 19. Furthermore, in the second pattern, the retention controller 16c controls to maintain a first piece of past maximum waveform information that is Doppler waveform information having been maximum waveform information before replaced with the latest maximum waveform information and a second piece of past maximum waveform information that is Doppler waveform information having been maximum waveform information before replaced with the first piece of past maximum waveform information.

The display controller 16d controls the monitor 2 to display one piece of the latest maximum waveform information and two pieces of past maximum waveform information as illustrated in FIG. 19. This enables the operator to select a Doppler waveform suitable for diagnosis from three Doppler waveforms and perform remeasurement processes, scroll processes, storage processes, and the like. For example, if the operator specifies the Doppler waveform information of one of the maximum waveform information and the past maximum waveform information displayed on the monitor 2, the display controller 16d controls the monitor 2 to display continuous Doppler waveforms including a Doppler waveform corresponding to the specified Doppler waveform (continuous Doppler waveforms for a period of one or more heart beats including a Doppler waveform corresponding to the specified Doppler waveform information).

With the second pattern above performed, the operator can securely acquire a Doppler waveform of the maximum flow velocity generated transiently.

Here, in a case where the second pattern is performed, maximum waveform information is updated by the processes performed by the detector 16a and the determination unit 16b described in the first embodiment. However, in a case where the second patter is performed, the detector 16a and the determination unit 16b may perform a first modification example or a second modification example as described below, not a peak hold process.

In the first modification example in the second pattern, the determination unit 16b compares peak flow velocities that are representative flow velocities sequentially output from the detector 16a with an average of peak flow velocities (average of the maximum flow velocities) that are representative flow velocities detected from each Doppler waveform corresponding to the maximum waveform information (latest maximum waveform information) and the past maximum waveform information retained in the Doppler waveform information data 15b.

Figure 20:
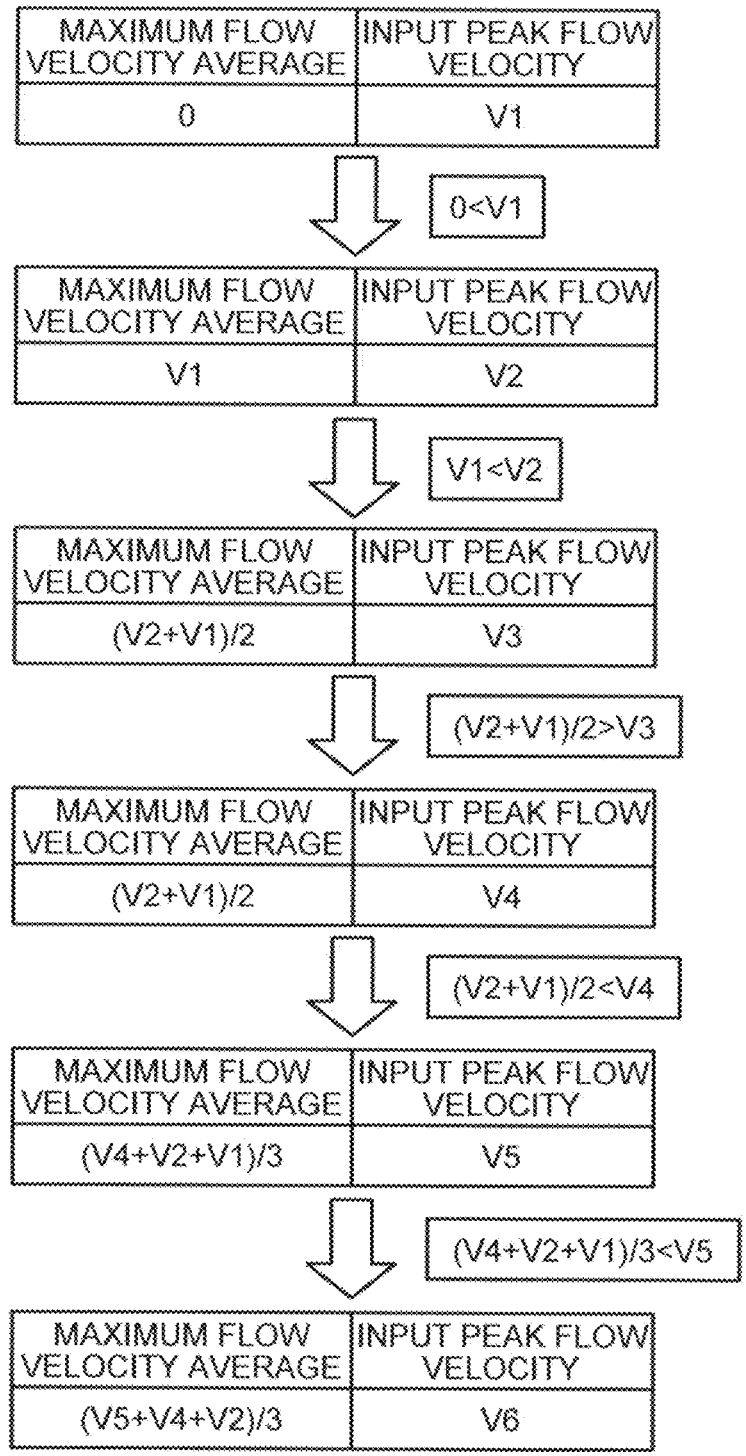

For example, as illustrated in FIG. 20, the determination 16b sets an initial value of the maximum flow velocity average to "0", and compares the initial value with "V1" that is a first peak flow velocity (input peak flow velocity) received from the detector 16a. The determination unit 16b updates the maximum flow velocity average to "V1" because "0<V1" as illustrated in FIG. 20. Thereafter the determination unit 16b compares "input peak flow velocity: V2" and "maximum flow velocity average: V1", and updates the maximum flow velocity average to "(V2+V1)/2" because "V1<V2" as illustrated in FIG. 20.

Furthermore, the determination unit 16b compares "input peak flow velocity: V3" and "maximum flow velocity average: (V2+V1)/2, and maintains the maximum flow velocity average as "(V2+V1)/2" because "(V2+V1)/2>3" as illustrated in FIG. 20. Thereafter, the determination unit 16b compares "input peak flow velocity: V4" and "maximum flow velocity average: (V2+V1)/2, and updates the maximum flow velocity average to "(V4+V2+V1)/3" because "(V2+V1)/2<V4" as illustrated in FIG. 20.

Furthermore, the determination unit 16b compares "input peak flow velocity: V5" and "maximum flow velocity average: (V4+V2+V1)/3, and updates the maximum flow velocity average to "(V5+V4+V2)/3" because "(V4+V2+V1)/3<V5" as illustrated in FIG. 20. Thereafter, the determination unit 16b compares "input peak flow velocity: V6" and "maximum flow velocity average: (V5+V4+V2)/3".

In the first modification example in the second pattern, the determination unit 16b determines the maximum flow velocity average at the present time point by sequentially comparing an input peak flow velocity and a maximum flow velocity average at the time point when the input peak flow velocity in question was detected, for example.

Furthermore, in the first modification example in the second patter, Doppler waveform information of Doppler waveform used for calculating the maximum flow velocity average at the present time point is retained in the Doppler waveform information data 15b as the latest maximum waveform information and past maximum waveform information.

Figure 21:
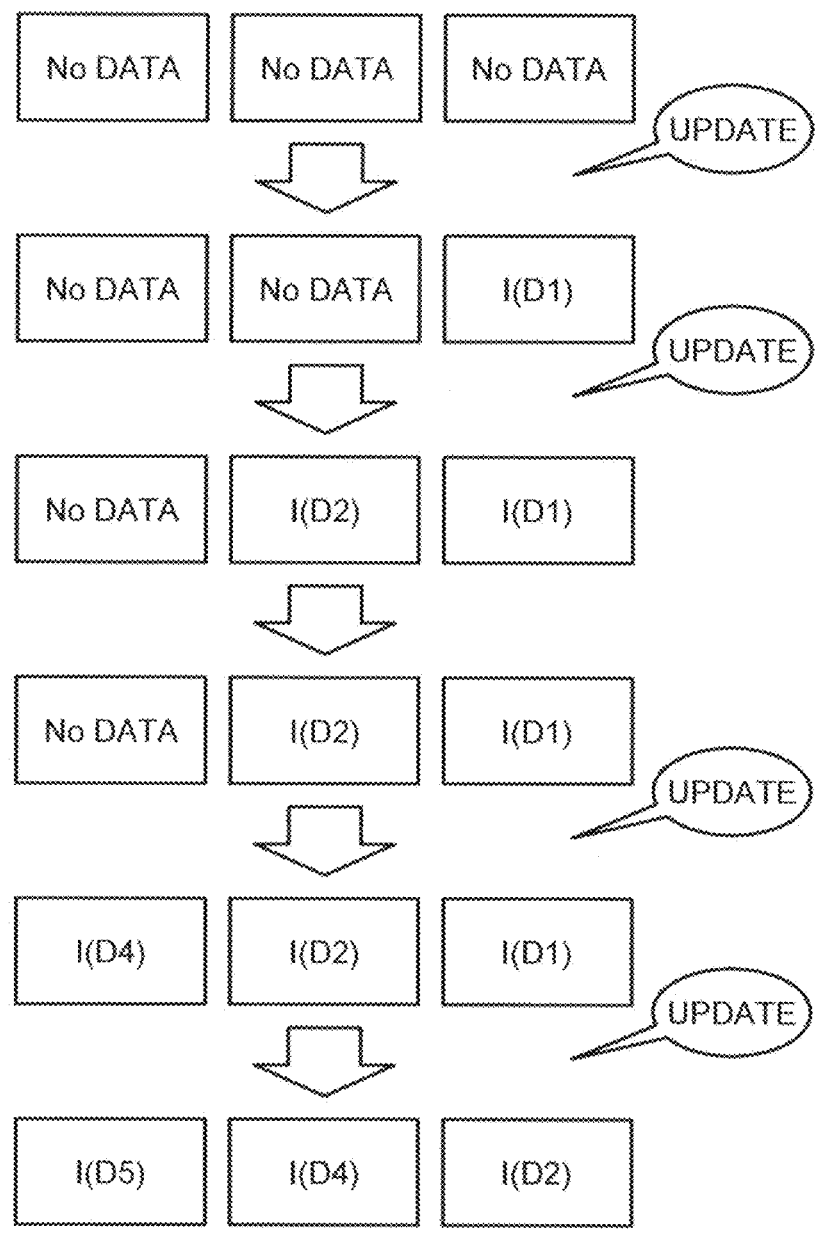

An example illustrated in FIG. 21 indicates processes performed by the retention controller 16c based on the results of the processes performed by the determination unit 16b exemplified in FIG. 20. It should be noted that the example illustrated in FIG. 21 presents three storage areas of the Doppler waveform information data 15b with three boxes, where the most right box stores therein the oldest Doppler waveform information and the most left box stores therein the latest Doppler waveform information. Furthermore, in the example illustrated in FIG. 21, when a new Doppler waveform is retained in a state that all the three storage areas of the Doppler waveform information data 15b retain Doppler waveform information, the oldest Doppler waveform information is discarded.

First, from the start of the Doppler waveform collection until the time point at which Doppler waveforms for a one heart beat period have not been collected, the three storage areas of Doppler waveform information data 15b are in a "No DATA" state as illustrated in FIG. 21. Next, if the maximum flow velocity average is updated to "V1", the retention controller 16c updates data to be retained by the Doppler waveform information data 15b to ["No DATA", "No DATA", "I(D1)"] as illustrated in FIG. 20.

Next, if the maximum average is updated to "(V2+V1)/2", the retention controller 16c updates the data to be retained by the Doppler waveform information data 15b to ["No DATA", "I(D2)", "I(D1)"] as illustrated in FIG. 21.

Next, if the maximum average of "(V2+V1)/2" is maintained, the retention controller 16c maintains the data to be retained by the Doppler waveform information data 15b as ["No DATA", "I(D2)", "I(D1)"].

Next, if the maximum average is updated to "(V4+V2+V1)/3", the retention controller 16c updates the data to be retained by the Doppler waveform information data 15b to ["I(D4)", "I(D2)", "I(D1)"] as illustrated in FIG. 21. Next, if the maximum average is updated to "(V5+V4+V2)/3", the retention controller 16c updates the data to be retained by the Doppler waveform information data 15b to ["I(D5)", "I(D4)", "I(D2)"] as illustrated in FIG. 21. In other words, the retention controller 16c discards the oldest "I(D1)" and newly retains "I(D5)" as illustrated in FIG. 21.

In the first modification example in the second pattern, both a case where the display controller 16d controls to display the latest maximum waveform information as maximum waveform information and a case where the display controller 16d controls to display average waveform information of the latest waveform information and past maximum waveform information as the maximum waveform information are acceptable. Furthermore, the display controller 16d controls to display the maximum waveform information in a sequentially updated manner in the display form described in the first embodiment or in the display form described in the second embodiment.

In the processes performed for the second modification example in the second pattern, the third embodiment and the first modification example in the second pattern are combined. In other words, the detector 16a calculates an average of representative flow velocities (an average of peak flow velocities, for example) of Doppler waveform for the latest predefined period (the latest one heart beat period) and of Doppler waveforms for at least one predefined period (at least a one heart beat period) collected immediately before the latest Doppler waveform in question. Furthermore, in the second modification example in the second pattern, the determination unit 16b compares the averages sequentially output from the detector 16a and an average of representative flow velocities (averages of peak flow velocities, for example) detected from each Doppler waveform corresponding to maximum waveform information and past maximum waveform information retained in the Doppler waveform information data 15b.

Figure 22:
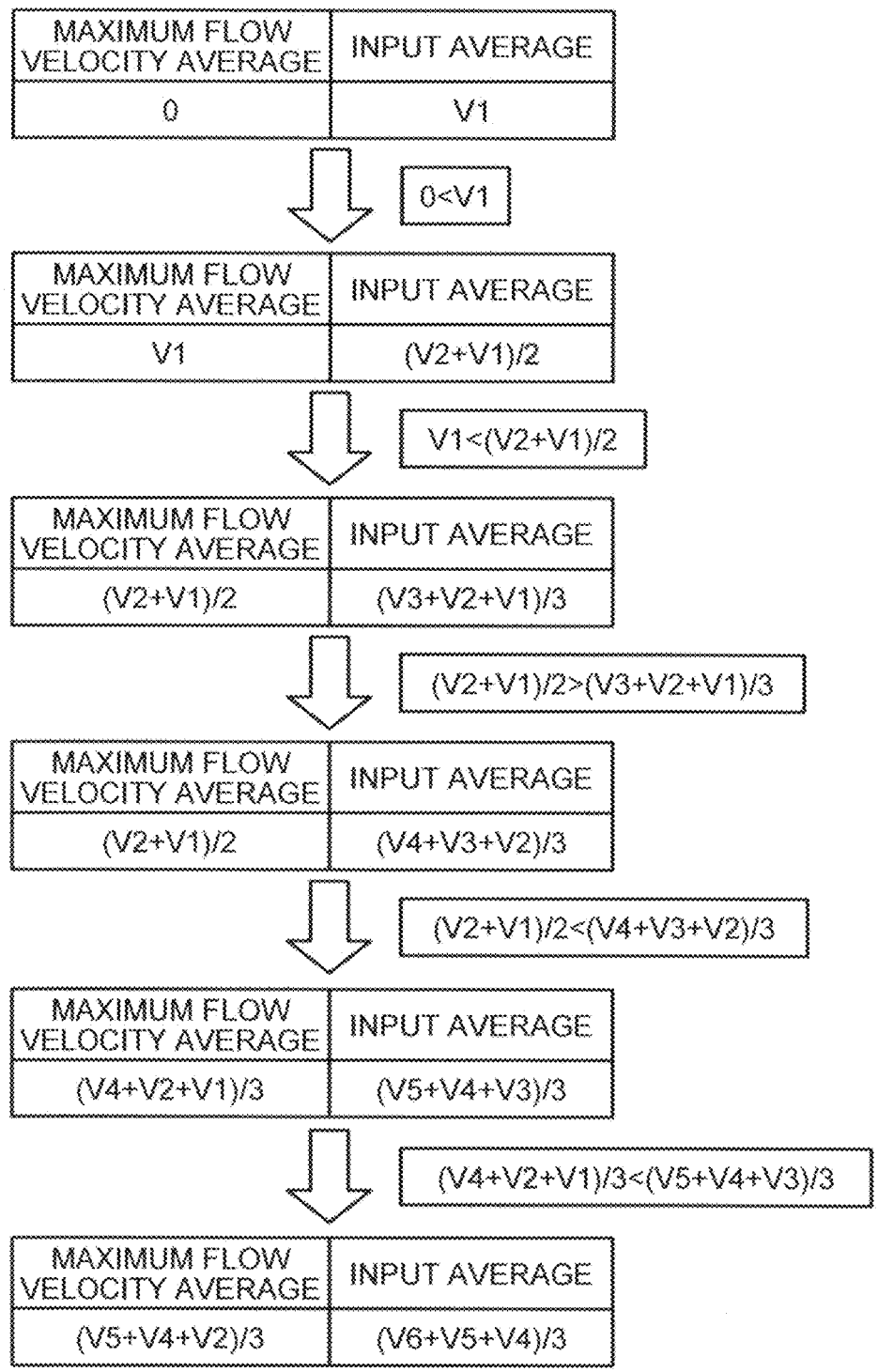

For example, as illustrated in FIG. 22, the determination unit 16b sets an initial value of the maximum flow velocity average to "0", and compares the initial value "0" and "V1" that is a first average (input average) received from the detector 16a. The determination unit 16b updates the maximum flow velocity average to "V1" because "0<V1" as illustrated in FIG. 22. Thereafter, the determination unit 16b compares "input average: (V2+V1)/2" and "maximum flow velocity average: V1", and updates the maximum flow velocity average to "(V2+V1)/2" because "V1<(V2+V1)/2" as illustrated in FIG. 22.

Furthermore, the determination unit 16b compares "input average: (V3+V2+V1)/3" and "maximum flow velocity average: (V2+V1)/2", and maintains the maximum flow velocity average as "(V2+V1)/2" because "(V2+V1)/2>(V3+V2+V1)/3" as illustrated in FIG. 22. Thereafter, the determination unit 16b compares "input average: (V4+V3+V2)/3" and "maximum flow velocity average: (V2+V1)/2", and updates the maximum flow velocity average because "(V2+V1)/2<(V4+V3+V2)/3" as illustrated in FIG. 22. For example, the determination unit 16b updates the maximum flow velocity average to "(V4+V2+V1)/3" by searching for a combination of three values from "V1 to V4" of which the average is the maximum.

Thereafter, the determination unit 16b compares "input average: (V5+V4+V3)/3" and "maximum flow velocity average: (V4+V2+V1)/3", and updates the maximum flow velocity average because "(V4+V2+V1)/3<(V5+V4+V3)/3" as illustrated in FIG. 22. For example, the determination unit 16b updates the maximum flow velocity average to "(V5+V4+V2)/3" by searching for a combination of three values from "V1 to V5" of which the average is the maximum. Thereafter, the determination unit 16b compares "input average: (V6+V5+V4)/3" and "maximum flow velocity average: (V5+V4+V2)/3".

In the second modification example in the second pattern, the determination unit 16b determines the maximum flow velocity average at the present time point by sequentially comparing an input average and a maximum flow velocity average at the time point when the input peak flow velocity in question was detected.

Here, the retention control processes performed by the retention controller 16c based on the results of the processes performed by the determination unit 16b exemplified in FIG. 22 will be in the same pattern in FIG. 21, and the explanations of the retention control processes are omitted.

Also in the second modification example in the second pattern, both a case where the display controller 16d controls to display the latest maximum waveform information as maximum waveform information and a case where the display controller 16d controls to display average waveform information of the latest waveform information and past maximum waveform information as the maximum waveform information are acceptable. Furthermore, the display controller 16d controls to display the maximum waveform information in a sequentially updated manner in the display form described in the first embodiment or in the display form described in the second embodiment.

By implementing the first modification example or the second modification example in the second pattern above, the operator can also securely acquire a Doppler waveform of the maximum flow velocity generated transiently. It should be noted that also in the fifth embodiment, when Doppler waveforms are collected through the PW method, a representative flow velocity detected by the detector 16a will be a peak flow velocity or an average flow velocity. Furthermore, when the reset process exemplified in FIG. 9B is performed in the fifth embodiment, all pieces of data retained in the Doppler waveform information data 15b are cleared.

In the first to the fifth embodiments, cases where the diagnosed part is a heart have been described. However, the processes described in the first to the fifth embodiments above may be applied to other diagnosed part than a heart. In such a case, a predefined period is not be limited to a one heart beat period but may be set to a one cycle period of breathing, or a one cycle period of motion in which an arm is moved up and down periodically.

In addition, "maximum waveform information" retained in the Doppler waveform information data 15b is not limited to information described in the first to the fifth embodiments above. For example, "maximum waveform information" may include "an array of measured values of Doppler signals for one heart beat" such as blood flow velocities, power of the blood flow, and variances of blood flow velocities measured from each Doppler signal extracted to generate Doppler waveforms for one heart beat, besides representative values measured from Doppler waveforms for one heart beat from which the maximum value was acquired such as PPG and VTI. Furthermore, "maximum waveform information" may include waveform information as "a shape of a waveform" of a Doppler waveform. As examples of such waveform information, a peak frequency value of an amplitude characteristic on a frequency axis obtained through frequency conversion of a time waveform and a phase value at a peak frequency will be suitable. Furthermore, "maximum waveform information" may include "information of a time when the maximum value was acquired". If such "information of time" is retained, the operator or the display controller 16d may read out Doppler waveforms for one heart beat from which the maximum value was acquired from a cine memory (image memory 15) using the "information of time" and display in parallel the Doppler waveforms thus acquired with Doppler waveforms that have been collected by the present time point, for example.

Out of the processes described in the first to the fifth embodiments, all or part of the processes described as automatic processes may be performed manually, and all or part of the processes described as manual processes may be performed automatically with a publically known method. In addition, information on processing procedures, control procedures, specific names, various data and parameters indicated in the description and drawings above may be changed as appropriate unless otherwise specified.

Furthermore, the components of the devices illustrated in the drawings indicate only functional concepts thereof, and the components need not to physically have the structures as illustrated in the drawings. In other words, specific forms of the dispersion and integration of the devices are not limited to those illustrated in the drawings, and all or part of the devices may be functionally or physically dispersed or integrated in any units in accordance with the load, use conditions, and the like for each device. Furthermore, all or any part of the processing functions performed in each device may be implemented in a CPU and a computer program analyzed and run by the CPU, or implemented as hardware based on wired logic.

Furthermore, the image processing methods described in the first to the fifth embodiments may be performed by running an image processing program prepared in advance on a computer such as a personal computer or a workstation. The program may be distributed via a network such as the Internet. Also, the program may be recorded in a computer-readable recording medium such as a hard disc, a flexible disc (FD), a compact disc read-only memory (CD-ROM), a magneto-optical disc (MO), and a digital versatile disc (DVD), and run when the program is read out from the recording medium.

As described above, it is possible to alleviate the burden on the operator collecting Doppler waveforms with the maximum peak flow velocity according to the first to the fifth embodiments.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
   a detector configured to detect a peak flow velocity of blood flow velocities acquired from Doppler waveforms collected in a time-serial manner or a peak value of average flow velocities of the blood flow velocities as a representative flow velocity for each of a plurality of predefined periods;
   a determination unit configured to determine a maximum value of a plurality of representative flow velocities by comparing, for the plurality of predefined periods, values of representative flow velocities sequentially output from the detector;
   a retention controller configured to control a predefined memory to retain maximum waveform information, which is Doppler waveform information that is information on Doppler waveforms, the maximum waveform information being Doppler waveform information collected in one period, of the plurality of predefined periods, in which the maximum value was detected by the determination unit; and
   a display controller configured to control a predefined display to display the maximum waveform information of the one period, which was retained in the predefined memory with Doppler waveform information having been collected by a present time point.

2. The ultrasound diagnostic apparatus according to claim 1, wherein
   the Doppler waveform information being maximum waveform information includes image data of a Doppler waveform corresponding to the Doppler waveform information and a measured value measured from the Doppler waveform, and
   the measured value includes at least one of a maximum flow velocity, a peak pressure gradient, a mean pressure gradient, an average flow velocity, and a velocity time integral.

3. The ultrasound diagnostic apparatus according to claim 2, wherein the detector is configured to detect the representative flow velocity by detecting an envelope or a gravity center velocity of the Doppler waveform and to calculate the measured value by using the envelope thus detected.

4. The ultrasound diagnostic apparatus according to claim 1, wherein the retention controller is configured to delete the maximum waveform information from the predefined memory when a predefined condition is satisfied.

5. The ultrasound diagnostic apparatus according to claim 4, wherein the retention controller is configured to delete the maximum waveform information when a predefined input unit receives a delete request from an operator.

6. The ultrasound diagnostic apparatus according to claim 4, wherein the retention controller is configured to delete the maximum waveform information every time a predetermined period has elapsed.

7. The ultrasound diagnostic apparatus according to claim 1, wherein the display controller is configured to set the same display scale for image data of a Doppler waveform corresponding to the maximum waveform information and image data of Doppler waveforms having been collected by the present time point and to display in parallel each piece of image data.

8. The ultrasound diagnostic apparatus according to claim 1, wherein the display controller is configured to set a different display scale for image data of a Doppler waveform corresponding to the maximum waveform information and image data of Doppler waveforms having been collected by the present time point.

9. The ultrasound diagnostic apparatus according to claim 1, wherein the retention controller is configured to output the maximum waveform information in a predefined file format to a predefined storage medium when receiving a request to store the maximum waveform information from an operator.

10. The ultrasound diagnostic apparatus according to claim 1, wherein the display controller is configured to control the predefined display to display continuous Doppler waveforms including a Doppler waveform corresponding to the maximum waveform information when receiving a request to display the maximum waveform information from an operator.

11. The ultrasound diagnostic apparatus according to claim 1, wherein
the detector is configured to calculate an average of representative flow velocities of latest Doppler waveforms for a given predefined period and representative flow velocities of Doppler waveforms for at least one predefined period having been collected immediately before the latest Doppler waveforms,
the determination unit is configured to determine a maximum average being a maximum average at the present time point by comparing averages sequentially output from the detector, and
the retention controller is configured to control the predefined memory to retain Doppler waveform information of the latest Doppler waveforms for the given predefined period out of Doppler waveforms for a second plurality of predefined periods from which the maximum average was detected as the maximum waveform information.

12. The ultrasound diagnostic apparatus according to claim 11, wherein the retention controller is configured to control the predefined memory to retain average waveform information averaged from Doppler waveform information of the Doppler waveforms for the second plurality of predefined periods from which the maximum average was calculated as the maximum waveform information.

13. The ultrasound diagnostic apparatus according to claim 1, wherein the retention controller is configured to control the predefined memory to retain Doppler waveform information for at least one of the predefined periods together with the maximum waveform information.

14. The ultrasound diagnostic apparatus according to claim 13, wherein the display controller is configured to control the predefined display to display Doppler waveform information of a plurality of Doppler waveforms retained in the predefined memory.

15. The ultrasound diagnostic apparatus according to claim 13, wherein the retention controller is configured to control the predefined memory to retain Doppler waveform information for a continuous plurality of predefined periods including the maximum waveform information.

16. The ultrasound diagnostic apparatus according to claim 13, wherein the retention controller is configured to control the predefined memory to maintain at least one piece of past maximum waveform information being Doppler waveform information having been maximum waveform information before the maximum waveform information, and retain the piece of past maximum waveform information together with the maximum waveform information.

17. The ultrasound diagnostic apparatus according to claim 16, wherein when an operator specifies Doppler waveform information of one of the maximum waveform information and the past maximum waveform information displayed on the predefined display, the display controller is configured to control the predefined display to display continuous Doppler waveforms including the Doppler waveform corresponding to the specified Doppler waveform information.

18. The ultrasound diagnostic apparatus according to claim 16, wherein the determination unit is configured compare the representative flow velocities sequentially output from the detector with an average of representative flow velocities detected from each Doppler waveform corresponding to the maximum waveform information and the past maximum waveform information retained in the predefined memory.

19. The ultrasound diagnostic apparatus according to claim 18, wherein
the detector is configured calculate an average of representative flow velocities of Doppler waveforms for a latest predefined period and representative flow velocities of Doppler waveforms for at least one predefined period collected immediately before the latest Doppler waveform, and
the determination unit is configured compare averages sequentially output from the detector and an average of representative flow velocities detected from each Doppler waveform corresponding to the maximum waveform information and the past maximum waveform information retained in the predefined memory.

20. An image processing method, comprising:
detecting, by a detector, a peak flow velocity of blood flow velocities acquired from Doppler waveforms collected in a time-serial manner or a peak value of average flow velocities of the blood flow velocities as a representative flow velocity for each of a plurality of predefined periods;
determining, by a determination unit, a maximum value of a plurality of representative values by comparing, for the plurality of predefined periods, values of representative flow velocities sequentially output from the detector;
controlling, by a retention controller, a predefined memory to retain maximum waveform information, which is Doppler waveform information that is information on Doppler waveforms, the maximum waveform information being Doppler waveform information collected in one period, of the plurality of predefined periods, in which the maximum value was detected by the determination unit; and
controlling, by a display controller, a predefined display to display the maximum waveform information of the one period, which was retained in the predefined memory with Doppler waveform information having been collected by a present time point.

* * * * *